US009560980B2

(12) United States Patent
Charlton et al.

(10) Patent No.: US 9,560,980 B2
(45) Date of Patent: Feb. 7, 2017

(54) AUTOMATIC SELECTION OF ELECTRODE VECTORS FOR ASSESSING RISK OF HEART FAILURE DECOMPENSATION EVENTS

(71) Applicant: Medtronic, Inc., Minneapolis, MN (US)

(72) Inventors: Sandra B. Charlton, Little Rock, AR (US); James J. Sims, Fayetteville, GA (US)

(73) Assignee: Medtronic, Inc., Minneapolis, MN (US)

( * ) Notice: Subject to any disclaimer, the term of this patent is extended or adjusted under 35 U.S.C. 154(b) by 152 days.

(21) Appl. No.: 13/752,623

(22) Filed: Jan. 29, 2013

(65) Prior Publication Data
US 2013/0197381 A1    Aug. 1, 2013

Related U.S. Application Data

(60) Provisional application No. 61/593,003, filed on Jan. 31, 2012.

(51) Int. Cl.
*A61B 5/0452* (2006.01)
*A61B 5/04* (2006.01)
(Continued)

(52) U.S. Cl.
CPC ......... *A61B 5/04011* (2013.01); *A61B 5/0538* (2013.01); *A61B 5/4875* (2013.01); *A61B 5/686* (2013.01); *A61B 5/7275* (2013.01)

(58) Field of Classification Search
CPC ..... A61B 5/053; A61B 5/7203; A61B 5/7221; A61B 5/0432
(Continued)

(56) References Cited

U.S. PATENT DOCUMENTS 4,737,382 A    4/1988 Katzman
5,117,824 A    6/1992 Keimel et al.
(Continued)

FOREIGN PATENT DOCUMENTS

EP    2 143 467 A1    1/2010
WO    2007111542 A1    10/2007
WO    2015057451 A1    4/2015

OTHER PUBLICATIONS

Khoury et al., "Ambulatory Monitoring of Congestive Heart Failure by Multiple Bioelectric Impedance Vectors," Journal of the American College of Cardiology, 2009;53:1075-81.

*Primary Examiner* — Michael Kahelin
*Assistant Examiner* — Minh Duc Pham
(74) *Attorney, Agent, or Firm* — Carol F. Barry

(57) ABSTRACT

An implantable medical device (IMD) is implanted in a patient. The IMD uses a plurality of electrode vectors to generate intrathoracic impedance measurements. The intrathoracic impedance measurements can be indicative of amounts of intrathoracic fluid in the patient. An accumulation of intrathoracic fluid may indicate that the patient is at an increased risk of experiencing a heart failure event in the near future. The IMD performs a vector selection operation on a recurring basis. When the IMD performs the vector selection operation, the IMD uses impedance measurements to select one of the electrode vectors. The IMD can perform a risk assessment operation on another recurring basis. During performance of the risk assessment operation, the IMD uses impedance measurements of the selected electrode vector and/or other patient characteristics stored within the IMD to determine whether the patient is at an increased risk of experiencing a heart failure event.

15 Claims, 11 Drawing Sheets

(51) Int. Cl.
*A61B 5/00* (2006.01)
*A61B 5/053* (2006.01)

(58) Field of Classification Search
USPC ........................................................ 600/523
See application file for complete search history.

(56) References Cited

U.S. PATENT DOCUMENTS

| | | | |
|---|---|---|---|
| 5,545,186 A | 8/1996 | Olson et al. | |
| 5,707,398 A | 1/1998 | Lu | |
| 5,752,976 A | 5/1998 | Duffin | |
| 5,755,736 A | 5/1998 | Gillberg et al. | |
| 5,836,975 A | 11/1998 | DeGroot | |
| 6,044,297 A | 3/2000 | Sheldon | |
| 6,104,949 A | 8/2000 | Pitts Crick et al. | |
| 6,250,309 B1 | 6/2001 | Krichen | |
| 6,418,346 B1 | 7/2002 | Nelson | |
| 6,480,745 B2 | 11/2002 | Nelson | |
| 6,512,940 B1 | 1/2003 | Brabec | |
| 6,522,915 B1 | 2/2003 | Ceballos | |
| 6,564,106 B2 | 5/2003 | Guck | |
| 6,622,046 B2 | 9/2003 | Fraley | |
| 6,795,733 B1 | 9/2004 | Lu | |
| 6,990,370 B1 | 1/2006 | Beatty et al. | |
| 7,010,347 B2 | 3/2006 | Schecter | |
| 7,272,442 B2 | 9/2007 | Freeberg | |
| 7,496,409 B2 | 2/2009 | Greenhut | |
| 7,623,909 B2 | 11/2009 | Sanghera et al. | |
| 7,630,763 B2 * | 12/2009 | Kwok et al. | 607/6 |
| 7,653,436 B2 | 1/2010 | Schecter | |
| 7,715,906 B2 | 5/2010 | Krause | |
| 7,720,529 B1 | 5/2010 | Schecter | |
| 7,904,153 B2 | 3/2011 | Greenhut | |
| 7,986,994 B2 | 7/2011 | Stadler et al. | |
| 7,996,072 B2 | 8/2011 | Haaefner | |
| 8,412,327 B2 | 4/2013 | Hou et al. | |
| 2003/0204214 A1 | 10/2003 | Ferek-Patric | |
| 2005/0080460 A1 | 4/2005 | Wang et al. | |
| 2005/0228276 A1 | 10/2005 | He et al. | |
| 2006/0253044 A1 * | 11/2006 | Zhang et al. | 600/512 |
| 2006/0253164 A1 | 11/2006 | Zhang et al. | |
| 2007/0156190 A1 | 7/2007 | Cinbas | |
| 2008/0027349 A1 | 1/2008 | Stylos | |
| 2008/0172100 A1 * | 7/2008 | Sanghera et al. | 607/30 |
| 2008/0183072 A1 | 7/2008 | Robertson et al. | |
| 2008/0269813 A1 | 10/2008 | Greenhut et al. | |
| 2008/0294218 A1 | 11/2008 | Savage et al. | |
| 2008/0319520 A1 | 12/2008 | Hill | |
| 2009/0076340 A1 | 3/2009 | Libbus | |
| 2009/0093857 A1 | 4/2009 | Markowitz et al. | |
| 2009/0275854 A1 * | 11/2009 | Zielinski et al. | 600/547 |
| 2010/0056884 A1 * | 3/2010 | Kwok et al. | 600/301 |
| 2010/0121415 A1 | 5/2010 | Skelton et al. | |
| 2010/0305641 A1 | 12/2010 | Pillai et al. | |
| 2011/0125049 A1 | 5/2011 | Nabutovsky et al. | |
| 2012/0221066 A1 | 8/2012 | Rosenberg et al. | |
| 2014/0214110 A1 * | 7/2014 | Yang et al. | 607/28 |
| 2015/0105835 A1 | 4/2015 | Thakur et al. | |

* cited by examiner

AUTOMATIC SELECTION OF ELECTRODE VECTORS FOR ASSESSING RISK OF HEART FAILURE DECOMPENSATION EVENTS

RELATED APPLICATION

The present application claims priority and other benefits from U.S. Provisional Patent Application Ser. No. 61/593,003, filed Jan. 31, 2012, entitled "AUTOMATIC SELECTION OF ELECTRODE VECTORS FOR ASSESSING RISK OF HEART FAILURE DECOMPOSITION EVENTS", incorporated herein by reference in its entirety.

TECHNICAL FIELD

This disclosure relates to implantable medical devices, and more particularly, to using an implantable medical device to determine a risk that a patient will experience a heart failure decompensation event.

BACKGROUND

Heart failure is a condition affecting thousands of people worldwide. Essentially, congestive heart failure occurs when the heart is unable to pump blood at an adequate rate to meet metabolic demand Heart failure may result in tissue congestion, peripheral edema, pulmonary edema, and shortness of breath. When heart failure is severe, it can lead to patient death.

Heart failure treatments have historically been pharmacologically based but more recently, biventricular stimulation has been added in moderate to severe heart failure patients meeting approved indications. Drug therapy has included diuretics, beta blockers, angiotensin converting enzyme inhibitors and aldosterone antagonists. Even though patients may follow strict drug regimens, heart failure exacerbations may arise, placing them at risk for increased morbidity and mortality.

Some implantable medical devices assist in detecting medical conditions based on measured impedance. For example, certain implantable medical devices are programmed to measure intrathoracic impedance of a patient. The intrathoracic impedance may be a function of the amount of fluid within the thoracic cavity of the patient. The amount of, or change in, the amount of fluid within the thoracic cavity may be indicative of various cardiac conditions. For instance, a relatively large amount, or a relatively significant change from the patient's average amount, of fluid within the thoracic cavity may be indicative of an acute heart failure event.

SUMMARY

This disclosure describes example techniques to identify the appropriate combination of electrodes to use for automatically selecting a representative intrathoracic impedance for a patient. A combination of electrodes the IMD uses to determine the intrathoracic impedance may be referred to herein as an electrode vector. The IMD can use intrathoracic impedance measurements from all of the available electrode vectors, a combination of multiple electrode vectors, or a single electrode vector to assess the risk that the patient may experience a heart failure decompensation event in the near future. The reliability of the intrathoracic impedance measurements for any given patient generated using the available electrode vectors is dynamic and may fluctuate over time with changing medical conditions and environmental factors. Therefore, the validity of a patient's risk of experiencing a heart failure decompensation event may be contingent upon a reliable intrathoracic impedance measurement.

As described in this disclosure, the IMD can perform a vector selection operation on a recurring basis. Whenever the IMD performs the vector selection operation, the IMD can select a given electrode vector. Intrathoracic impedance measurements generated using the given electrode vector may be more reliable than intrathoracic impedance measurements generated using either a default vector or a previously selected electrode vector. Subsequently, the IMD may determine the risk based, at least in part, on the transthoracic impedance measurements generated using the electrode vector selected during the vector selection operation. Because the IMD may automatically perform the vector selection operation, it may be unnecessary for a clinician or other person to manually select which electrode vector is utilized in determining the risk that a patient will experience a heart failure decompensation event in the near future.

One example embodiment is a method for determining a risk of a patient experiencing a heart failure decompensation event in the near future. The method comprises using, by a medical device implanted in the patient, a plurality of electrode vectors to generate a plurality of intrathoracic impedance measurements. Each of the electrode vectors is a different combination of electrodes. The method also comprises performing, by the medical device, a vector selection operation on a first recurring basis. Each time the medical device performs the vector selection operation, the medical device selects a given electrode vector from among the plurality of electrode vectors. The intrathoracic impedance measurements generated using the given electrode vector are at a current time likely to be more reliable than the intrathoracic impedance measurements generated using other ones of the electrode vectors for determining the risk. The method also comprises performing, by the medical device, a risk assessment operation on a second recurring basis. Each time the medical device performs the risk assessment operation, the medical device determines the risk based at least in part on intrathoracic impedance measurements generated using one of the electrode vectors that was selected during a most recent performance of the vector selection operation.

In another embodiment, an implantable medical device (IMD) is implanted in a patient. The IMD comprises a plurality of electrodes and a processor. The processor is configured to use a plurality of electrode vectors to generate a plurality of intrathoracic impedance measurements. Each of the electrode vectors is a different combination of the electrodes. The processor is also configured to perform a vector selection operation on a first recurring basis. Each time the processor performs the vector selection operation, the processor selects a given electrode vector from among the plurality of electrode vectors. The intrathoracic impedance measurements generated using the given electrode vector are at a current time likely to be more reliable than the intrathoracic impedance measurements generated using other ones of the electrode vectors for determining the risk. The processor is also configured to perform a risk assessment operation on a second recurring basis. Each time the processor performs the risk assessment operation, the processor determines the risk based at least in part on intrathoracic impedance measurements generated using one of the electrode vectors that was selected during a most recent performance of the vector selection operation.

The details of one or more examples according to the present disclosure are set forth in the accompanying drawings and the description below. Other features, objects, and advantages will be apparent from the description and drawings, and from the claims.

DETAILED DESCRIPTION

Figure 1:
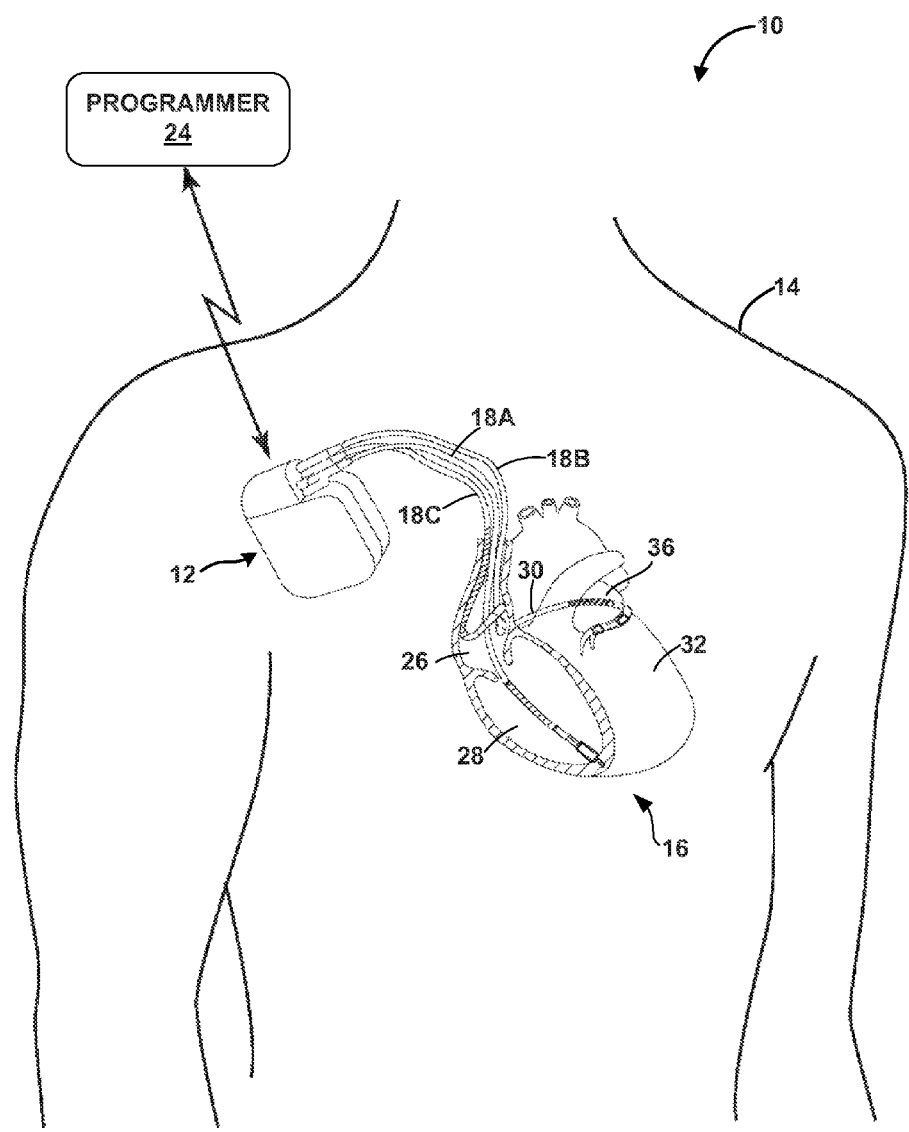
FIG. 1 is a conceptual drawing that illustrates an example system in which an implantable medical device (IMD) is implanted in a patient.

Congestive heart failure may occur gradually over time due to heart disease, patient inactivity, cardiac arrhythmias, hypertension, and other conditions. Nevertheless, certain heart failure decompensation events can lead to a relatively rapid worsening of a patient's condition, precipitate hospitalization and, in some cases, can cause the patient's death. It may not be possible for health care professionals to always personally monitor the patient for an increased risk of a heart failure decompensation event. However, certain patient metrics can be monitored automatically. These patient metrics can be used to determine whether the patient is at an increased risk for a heart failure decompensation event.

As described in this disclosure, an implantable medical device (IMD) is implanted into a patient. The IMD may collect and store patient metrics. The patient metrics include data regarding the patient. Such patient metrics can include, but are not limited to, therapy use statistics (e.g., pacing or shock delivery), intrathoracic impedance, heart rate, heart rate variability, patient activity, weight, blood pressure, respiration rate, sleep apnea burden derived from respiration rate, temperature, ischemia burden, sensed cardiac event intervals, cardiac events, and other information about the patient. Example cardiac events may include atrial fibrillation, ventricular rate during atrial fibrillation, or ventricular tachyarrhythmias. The concentration or levels of various substances, such as troponin and/or brain natriuretic peptide (BNP) levels, within the patient may also be patient metrics.

The IMD can use the patient metrics to determine a risk that the patient will suffer a heart failure decompensation event in the near future. For instance, IMD can use the patient metrics to determine the risk that the patient will experience a heart failure decompensation event within the next several hours or days, e.g., 12 hours, 24 hours, 72 hours, etc. In some instances, treatment of the heart failure decompensation event may require hospitalization of the patient. A patient experiences a heart failure decompensation event when the patient's heart is unable to pump a sufficient amount of blood to the patient's tissues to meet the patient's metabolic demands.

In various examples, the IMD can determine this risk in various ways. For example, the IMD can perform a risk assessment operation to determine the risk. During performance of the risk assessment operation, the IMD uses one or more patient metrics to determine the risk. One or more of these patient metrics can be based on the patient's intrathoracic impedance. If the IMD detects that the patient's risk of experiencing a heart failure decompensation event in the near future is sufficiently high, has increased from recently assessed risk averages, or deviates from their threshold-level risk, the IMD may deliver patient metrics and/or other information to healthcare professionals and/or the patient.

The IMD can include or be coupled to one or more sensing devices that collect the patient metrics. For example, the IMD can be coupled to one or more leads implanted within the heart of the patient. Each one of the leads may include one or more electrodes. The housing of the implantable medical device may also include one or more electrodes. To collect data regarding the patient's intrathoracic impedance, the IMD may apply a voltage across two of the electrodes, measure the current flowing through the electrodes (e.g., from one electrode into the other electrode), and divide the value of the applied voltage by the value of the measured current to determine the intrathoracic impedance. In another example, the IMD may apply a known current across two of the electrodes, measure the voltage between the electrodes, and divide the measured voltage by the applied current to measure the intrathoracic impedance.

The IMD can collect multiple intrathoracic impedance values by applying voltages across different combinations of the electrodes. This disclosure can refer to the combinations of electrodes as "electrode vectors." Some of the electrode vectors may generate intrathoracic impedance measurements that are more reliable for determining risks of heart failure decompensation events than other ones of the electrode vectors. Moreover, the electrode vector that generates intrathoracic impedance measurements that are most reliable or consistent may change over time. This may be due to change in the size of the patient's heart, variability of location of fluid accumulation within the patient's chest, location of the IMD, and so on. Furthermore, in different patients different electrode vectors may generate intrathoracic measurements that are most reliable. For example, intrathoracic fluid may accumulate in different locations in different patients. In this example, different electrode vectors may be better at detecting fluid accumulation in different locations. In another example, particular anatomical aspects of different patients may make certain different electrode vectors more reliable. Such anatomical aspects can include shape and size of patients' organs, prosthetics used by patients, and so on.

Accordingly, the IMD can perform a vector selection operation. When the IMD performs the vector selection operation, the IMD uses intrathoracic impedance measurements from the electrode vectors to select a given electrode vector. The intrathoracic impedance measurements generated using the given electrode vector may, at the current time, be more reliable than the intrathoracic impedance measurements generated using other ones of the electrode vectors in determining the risk that the patient will experience a heart failure decompensation event in the near future. For instance, the IMD may more frequently determine the risk reliably when the IMD uses the intrathoracic impedance measurements generated using the given electrode vector than when using intrathoracic impedance measurements generated using other ones of the electrode vectors. This reliability, for instance, may be based on previous acute heart failure decompensation events for the patient when specific electrode vectors were utilized.

FIG. 1 is a conceptual drawing that illustrates an example system 10 in which an implantable medical device (IMD) 12 is implanted in a patient 14. IMD 12 is configured to determine a risk of patient 14 experiencing a heart failure decompensation event in the near future. In various examples, IMD 12 may comprise various types of IMDs. For example, IMD 12 may be an implantable pacemaker, cardioverter defibrillator, and/or another type of IMD that provides electrical signals to a heart 16 of patient 14.

In the example of FIG. 1, patient 14 is a human. Nevertheless, readers will understand that in other examples, patient 14 can be another type of animal. For example, patient 14 can be a monkey, an ape, a dog, a cow, or another type of animal.

IMD 12 is coupled to a right ventricular (RV) lead 18A, a left ventricular (LV) lead 18B, and a right atrial (RA) lead 18C (collectively, "leads 18"). Leads 18 extend into heart 16. In the example shown in FIG. 1, RV lead 18A extends through one or more veins (not shown), the superior vena cava (not shown), a right atrium 26 of heart 16, and into a right ventricle 28 of heart 16. LV lead 18B extends through one or more veins, the vena cava, a right atrium 26 of heart 16, and into a coronary sinus 30 to a region adjacent to the free wall of left ventricle 32 of heart 16. RA lead 18C extends through one or more veins and the vena cava, and into the right atrium 26 of heart 16.

IMD 12 can use leads 18 to sense electrical activity of heart 16. For example, IMD 12 can use leads 18 to sense electrical signals attendant to the depolarization and repolarization of heart 16. Furthermore, IMD 12 can use leads 18 to deliver electrical stimulation to heart 16. In various examples, IMD 12 can use leads 18 to deliver various types of electrical stimulation to heart 16. For example, IMD 12 can use leads 18 to provide pacing pulses to heart 16 based on the received electrical signals. In another example, IMD 12 can use the received electrical signals to detect arrhythmia of heart 16, such as tachycardia or fibrillation of atria 26 and 36 and/or ventricles 28 and 32. In this example, IMD 12 can provide defibrillation therapy and/or cardioversion therapy via electrodes located on at least one of leads 18. In this example, IMD 12 may be programmed to deliver a progression of therapies, e.g., pulses with increasing energy levels, until the arrhythmia of heart 16 is terminated. IMD 12 may employ one or more arrhythmia detection techniques known in the art to detect the arrhythmia.

In addition, IMD 12 use leads 18 and other data sources to collect patient metric data. IMD 12 can use the patient metric data to determine whether patient 14 is at an increased risk of experiencing a heart failure decompensation event in the near future. IMD 12 can perform an alert operation upon determining that patient 14 is at an increased risk of experiencing a heart failure decompensation event in the near future. The alert operation can alert one or more people of the increased risk of the heart failure risk.

In various examples, IMD 12 can collect patient metrics that comprise various types of information about patient 14. For example, the patient metrics may include intracardiac or intravascular pressure or volume, a thoracic fluid index, activity, posture, respiration, an atrial tachycardia or fibrillation burden, a ventricular contraction rate during atrial fibrillation, a nighttime heart rate, a heart rate variability, a cardiac resynchronization therapy percentage, a bradyarrhythmia pacing therapy percentage (in a ventricle and/or atrium), electrical shock events, blood pressure, sleep apnea, lung volume, lung density, breathing rate, and/or other information regarding patient 14. In some examples, the atrial tachycardia or fibrillation burden may be a time of the event, a percent or amount of time over a certain period, a number of episodes, or even a frequency of episodes. IMD 12 can use leads 18 to generate an electrogram. Patient metrics such as respiration rates and sleep apnea may be detectable via the electrogram. As described in detail below, IMD 12 can also use leads 18 to detect intrathoracic impedance values indicative of fluid volume in patient 14.

IMD 12 may communicate with a programmer 24. Programmer 24 comprises one or more computing devices that are external to patient 14. In various examples, programmer 24 can comprise various types of computing devices. For example, programmer 24 can comprise a handheld computing device, a computer workstation, a tablet computer, a desktop computer, a smartphone, a laptop computer, a server computer, a mainframe computer, or another type of networked computing device. In various examples, IMD 12 and programmer 24 may communicate via various wireless communication techniques known in the art. Example communication techniques may include, but are not limited to, low frequency or radiofrequency (RF) telemetry. In some examples, programmer 24 may include a programming head that may be placed proximate to the body of patient 14 near an implant site of IMD 12 in order to improve the quality and/or security of communication between IMD 12 and programmer 24.

A user may interact with programmer 24. In various examples, the user can interact with programmer 24 in various ways. For example, programmer 24 may include a user interface. In this example, the user may interact with programmer 24 via the user interface. In other examples, the user may interact with programmer 24 remotely via a networked computing device. In various examples, various people can use programmer 24. For example, a physician, technician, surgeon, electrophysiologist, or another healthcare professional can use programmer 24. In other examples, patient 14 may use programmer 24.

The user may interact with programmer 24 to review various types of information received from IMD 12. For example, the user may interact with programmer 24 to review physiological or diagnostic information from IMD 12. In another example, the user may use programmer 24 to review patient metric data received from IMD 12. In yet another example, the user may use programmer 24 to review a heart failure risk score. The heart failure risk score may have a value that is correlated with a risk or likelihood that patient 14 will experience a heart failure decompensation event. In yet another example, the user may use programmer 24 to review an alert. Programmer 24 may present the alert when patient 14 is at an increased risk of experiencing a heart failure decompensation event. In yet another example, the user may use programmer 24 to review information received from IMD 12 regarding the performance or integrity of IMD 12 or other components of system 10, such as leads 18 or a power source of IMD 12. In some examples, any of this information may be presented to the user as an alert (e.g., a notification or instruction). IMD 12 may push alerts to programmer 24 in order to facilitate alert delivery.

The user may interact with programmer 24 to perform various configuration operations on IMD 12. For example, a user may interact with programmer 24 to select values for operational parameters of IMD 12. The user may also interact with programmer 24 to configure how IMD 12 senses, detects, and manages patient metrics. For example, the user may configure the frequency of sampling or the evaluation window used to monitor the patient metrics. In another example, the user may interact with programmer 24 to configure IMD 12 to use a particular combination of electrodes when determining an intrathoracic impedance. In another example, the user may interact with programmer 24 to set metric thresholds used to monitor the status of patient metrics. IMD 12 can compare patient metrics to the metric thresholds to determine whether patient 14 is at an increased risk of a potential heart failure decompensation event.

Figure 2:
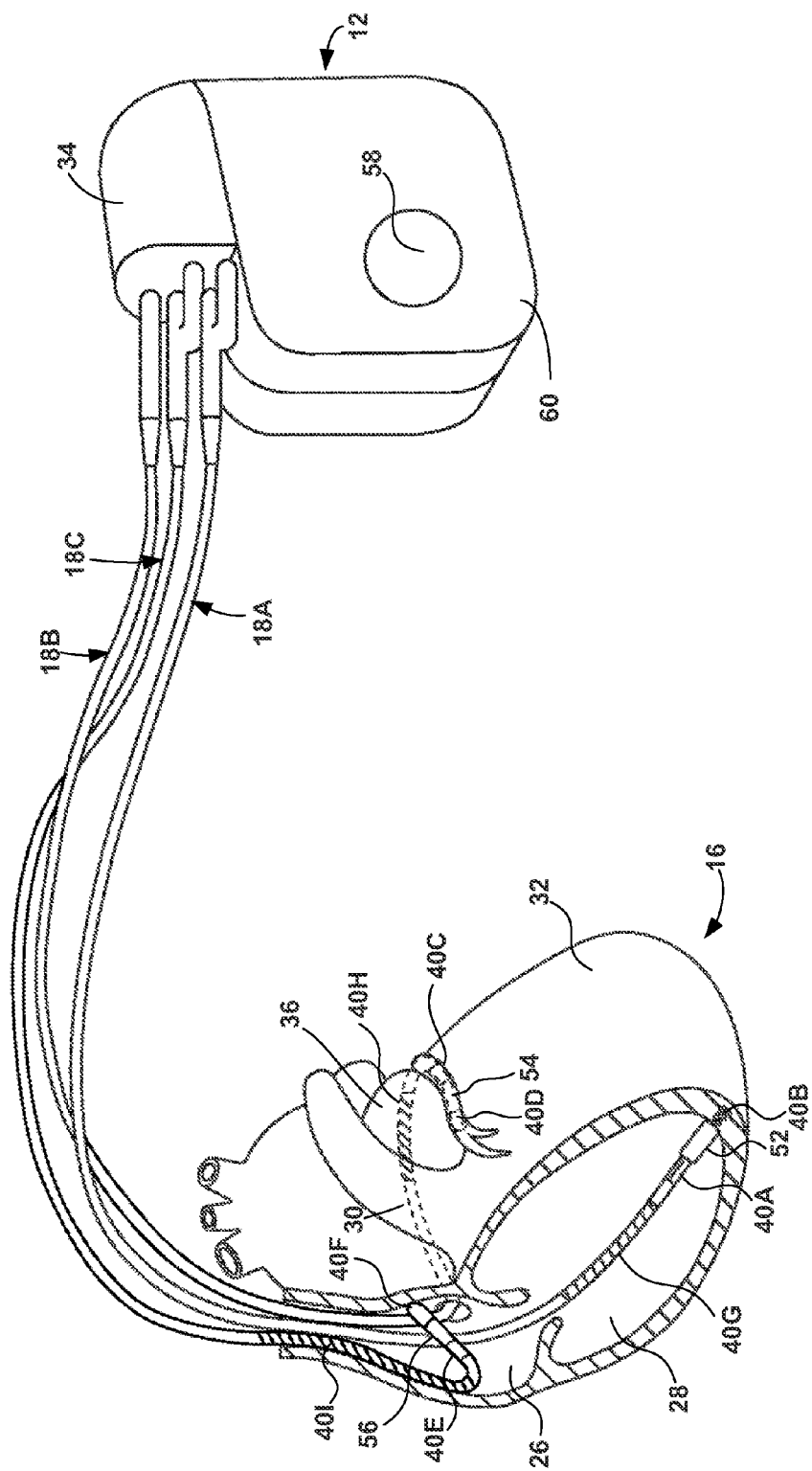
FIG. 2 is a conceptual drawing that illustrates an example configuration of the IMD and leads in greater detail.

FIG. 2 is a conceptual drawing that illustrates an example configuration of IMD 12 and leads 18 in greater detail. As shown in FIG. 2, IMD 12 comprises housing 60 and a connector block 34. Housing 60 provides a hermetic seal around IMD 12. Connector block 34 electrically couples IMD 12 to leads 18. In various examples, connector block 34 electrically couples leads 18 to IMD 12 in various ways. For example, proximal ends of leads 18 may include electrical contacts that electrically couple to respective electrical contacts within connector block 34 of IMD 12. In addition, in some examples, leads 18 may be mechanically coupled to connector block 34 with the aid of set screws, connection pins, snap connectors, or another suitable mechanical coupling mechanism.

Each of leads 18 comprises an elongated insulative lead body. The lead bodies of leads 18 may carry a number of concentric coiled conductors separated from one another by tubular insulative sheaths. In addition, leads 18 comprise electrodes 40A-40I (collectively, "electrodes 40"). Each of the electrodes 40 may be electrically coupled to a respective one of the coiled conductors within the lead body of its associated lead 18, and thereby coupled to respective ones of the electrical contacts on the proximal end of leads 18.

Bipolar electrodes 40A and 40B are located adjacent to a distal end of RV lead 18A in right ventricle 28. Bipolar electrodes 40C and 40D are located adjacent to a distal end of LV lead 18B in coronary sinus 30. Bipolar electrodes 40E and 40F are located adjacent to a distal end of RA lead 18C in right atrium 26. In the illustrated example, there are no electrodes located in left atrium 36. However, other examples may include electrodes in left atrium 36.

In various examples, electrodes 40 may take various forms. For example, electrodes 40A, 40C and 40E may take the form of ring electrodes. Electrodes 40B, 40D and 40F may take the form of extendable helix tip electrodes mounted retractably within insulative electrode heads 52, 54 and 56, respectively. In other examples, one or more of electrodes 40B, 40D and 40F may take the form of small circular electrodes at the tip of a tined lead or other fixation element. Electrodes 40G, 40H and 40I may be elongated and may take the form of a coil.

As illustrated in FIG. 2, IMD 12 can include one or more housing electrodes, such as housing electrode 58. Housing electrode 58 may be formed integrally with an outer surface of housing 60 of IMD 12 or otherwise coupled to housing 60. In some examples, housing electrode 58 is defined by an uninsulated portion of an outward facing portion of housing 60 of IMD 12. Other divisions between insulated and uninsulated portions of housing 60 may be employed to define two or more housing electrodes. In some examples, housing electrode 58 comprises substantially all of housing 60.

IMD 12 may sense electrical signals attendant to the depolarization and repolarization of heart 16 via electrodes 40. The electrical signals are conducted to IMD 12 from electrodes 40 via leads 18. IMD 12 may sense such electrical signals via any bipolar combination of electrodes 40. Furthermore, IMD 12 may use electrodes 40 for unipolar sensing in combination with housing electrode 58. This disclosure can refer to the combination of electrodes as an electrode vector.

Furthermore, IMD 12 may use electrodes 40 to deliver therapies to heart 16. For example, IMD 12 can deliver pacing pulses via bipolar combinations of electrodes 40A, 40B, 40C, 40D, 40E and 40F to produce depolarization of cardiac tissue of heart 16. In some examples, IMD 12 delivers pacing pulses via any of electrodes 40A, 40B, 40C, 40D, 40E and 40F in combination with housing electrode 58 in a unipolar configuration. Furthermore, IMD 12 may deliver defibrillation pulses to heart 16 via any combination of electrodes 40G, 40H, 40I, and housing electrode 58.

In some examples, IMD 12 may use electrodes 58, 40G, 40H, and 40I to deliver cardioversion pulses to heart 16. Electrodes 40G, 40H, and 40I may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

IMD 12 may use any of electrodes 40 and 58 to sense or detect patient metrics. Typically, IMD 12 may detect and collect patient metrics from those electrode vectors used to treat patient 14. For example, IMD 12 may derive an atrial fibrillation duration, heart rate, and heart rate variability metrics from electrograms generated to deliver pacing therapy. However, IMD 12 may utilize other electrode vectors to detect these types of metrics from patient 14 when other electrical signals may be more appropriate for therapy.

In addition, IMD 12 may use electrodes 40 and 58 to sense non-cardiac signals. For example, two or more electrodes may be used to measure an impedance within the thoracic cavity of patient 14. IMD 12 may use this intrathoracic impedance to generate a fluid index patient metric that indicates the amount of fluid accumulation within patient 14. Since a greater amount of fluid may indicate increased pumping loads on heart 16, the fluid index may be used as an indicator of heart failure risk. IMD 12 may periodically measure the intrathoracic impedance to identify a trend in the fluid index over days, weeks, months, and even years of patient monitoring.

In general, the two electrodes used to measure the intrathoracic impedance may be located at two different positions within the chest of patient 14. For example, IMD 12 may use electrode 40G and housing electrode 58 as the electrode vector for intrathoracic impedance because electrode 40G is located within right ventricle 28 and housing electrode 58 is located at the implant site of IMD 12 generally in the upper chest region. However, other electrodes spanning multiple organs or tissues of patient 14 may also be used, e.g., an additional implanted electrode used only for measuring intrathoracic impedance.

As the tissues within the thoracic cavity of patient 14 increase in fluid content, the impedance between two electrodes may also change. For example, the impedance between an RV coil electrode and the housing electrode 58 may be used to monitor changing intrathoracic impedance. An example system for measuring intrathoracic impedance is described in U.S. Pat. No. 6,104,949 to Pitts Crick et al., entitled, "MEDICAL DEVICE," which issued on Aug. 15, 2000 and is incorporated herein by reference in its entirety. IMD 12 may use this impedance to create a fluid index. As the fluid index increases, more fluid is being retained within patient 14 and heart 16 may be stressed to keep up with metabolic demands. Therefore, this fluid index may be a patient metric used to determine the risk that patient 14 will experience a heart failure decompensation event in the near future.

The configuration of system 10 illustrated in FIGS. 1 and 2A is merely one example. In other examples, system 10 can include more or fewer leads or lead segments. For example, IMD 12 can be coupled to a lead that deploys one or more electrodes within the vena cava, or other veins. For example, system 10 may include epicardial leads and/or subcutaneous leads instead of or in addition to the transvenous leads 18 illustrated in FIG. 1. In this example, the epicardial leads and/or subcutaneous leads may deploy electrodes implanted outside of heart 16. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to measure intrathoracic impedance as a patient metric for identifying a heart failure risk. Furthermore, in some examples, IMD 12 does not use leads for pacing or sensing. In such examples, IMD 12 may measure intrathoracic impedance using electrodes that are not deployed on leads.

Further, IMD 12 need not be implanted within patient 14. In examples in which IMD 12 is not implanted in patient 14, IMD 12 may sense electrical signals and/or deliver defibrillation pulses and other therapies to heart 16 via percutaneous leads that extend through the skin of patient 14 to a variety of positions within or outside of heart 16. Further, external electrodes or other sensors may be used by IMD 12 to deliver therapy to patient 14 and/or sense and detect patient metrics used to generate a heart failure risk score.

Figure 4:
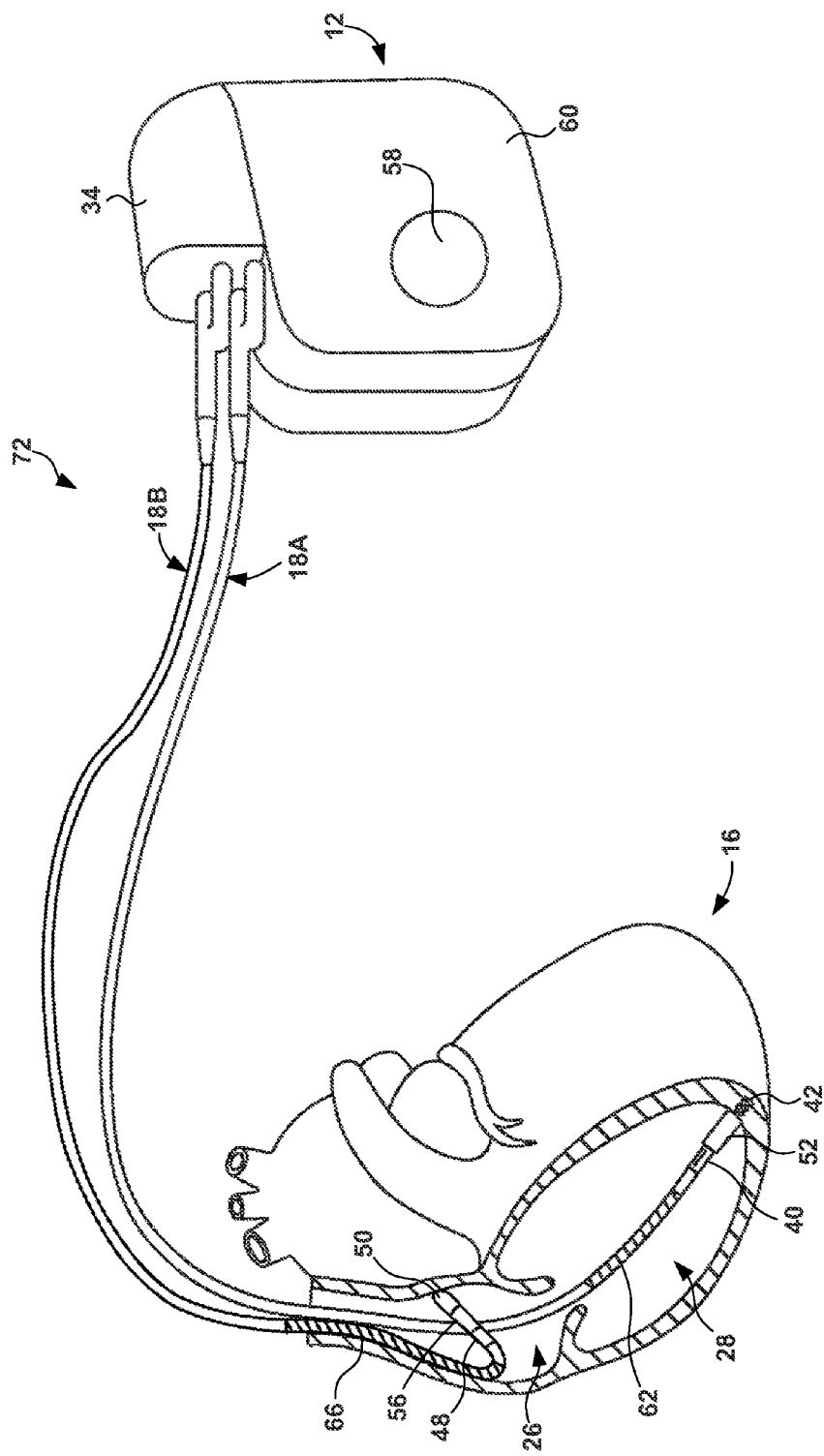
FIG. 4 is a conceptual diagram that illustrates an example system, which is similar to the system of FIGS. 1-3, but includes two leads, rather than three.

In addition, in other examples, a system may include any suitable number of leads coupled to IMD 12, and each of the leads may extend to any location within or proximate to heart 16. For example, other systems may include three transvenous leads located as illustrated in FIGS. 1 and 2, and an additional lead located within or proximate to left atrium 36. As another example, other systems may include a single lead that extends from IMD 12 into right atrium 26 or right ventricle 28, or two leads that extend into a respective one of the right ventricle 28 and right atrium 26. An example of a two lead type of system is shown in FIG. 4. Any electrodes located on these additional leads may be used in sensing and/or stimulation configurations.

Figure 3:
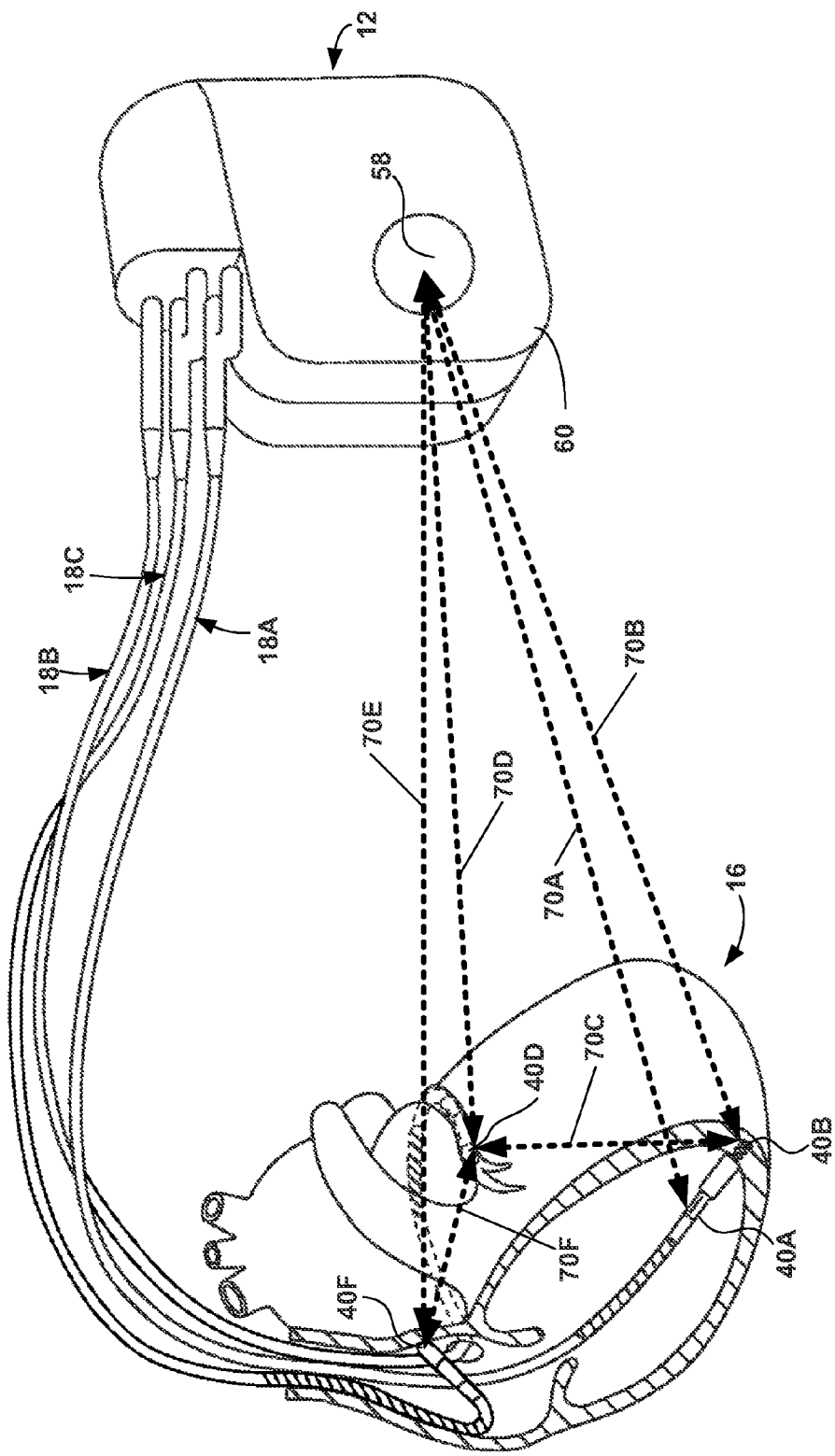
FIG. 3 is a conceptual diagram that illustrates example electrode vectors.

FIG. 3 is a conceptual diagram that illustrates example electrode vectors 70A-70F (collectively, "electrode vectors 70") superimposed on the configuration of IMD 12 illustrated in FIG. 2. Electrode vector 70A extends from electrode 40A to housing electrode 58. Electrode vector 70B extends from electrode 40B to housing electrode 58. Electrode vector 70C extends from electrode 40B to electrode 40D. Electrode vector 70D extends from electrode 40D to housing electrode 58. Electrode vector 70E extends from electrode 40F to housing electrode 58. Electrode vector 70F extends from electrode 40D to electrode 40F. Other examples can include other electrode vectors.

FIG. 4 is a conceptual diagram that illustrates an example system 72. System 72 is similar to system 10 of FIGS. 1-3, but includes two leads 18A and 18B, rather than three leads. Leads 18A and 18B are implanted within right ventricle 28 and right atrium 26, respectively. System 72 may be useful for physiological sensing and/or providing pacing, cardioversion, or other therapies to heart 16. Accumulation of interthoracic fluid may be detected according in two lead systems in the manner described herein with respect to three lead systems. In other examples, a system similar to systems 10 and 72 may only include one lead (e.g., any of leads 18) to deliver therapy and/or sensor and detect patient metrics related to monitoring risk of heart failure.

Figure 5:
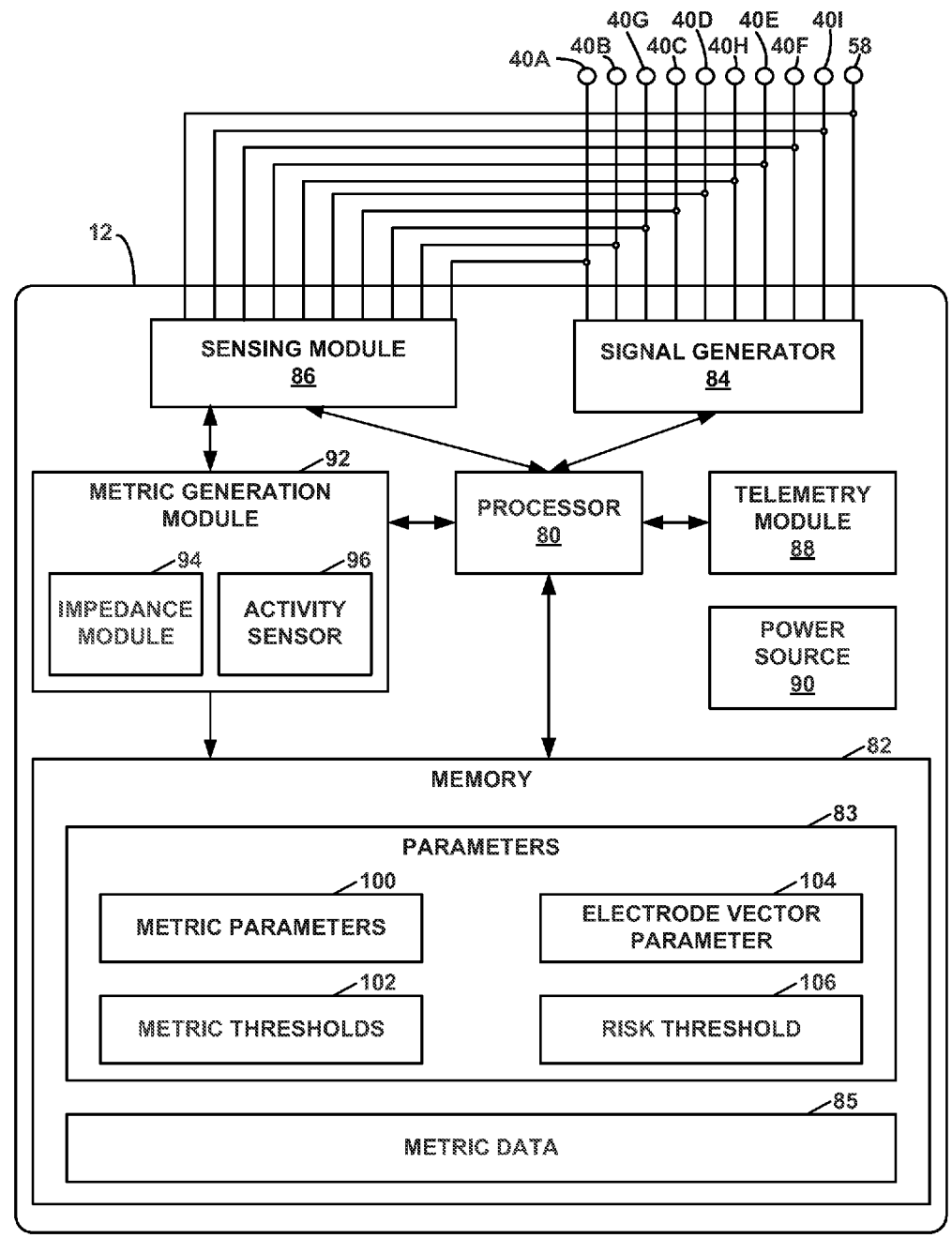
FIG. 5 is a functional block diagram that illustrates an example configuration of the IMD.

FIG. 5 is a functional block diagram that illustrates an example configuration of IMD 12. In the illustrated example, IMD 12 includes a processor 80, a memory 82, a metric generation module 92, a signal generator 84, a sensing module 86, a telemetry module 88, and a power source 90. Readers will understand that other examples of IMD 12 may include more, fewer, or different functional components.

Processor 80 comprises one or more logic circuits that process data. In various examples, processor 80 may comprise logic circuits of various types. For example, processor 80 may comprise one or more of microprocessors, controllers, digital signal processors (DSPs), application specific integrated circuits (ASICs), field-programmable gate arrays (FPGAs), or another type of discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry.

Memory 82 comprises one or more computer storage media that stores data for subsequent retrieval. Example types of computer storage media include, but are not limited to, volatile, non-volatile, magnetic, optical, or electrical media, such as a random access memory (RAM), read-only memory (ROM), non-volatile RAM (NVRAM), electrically-erasable programmable ROM (EEPROM), flash memory, or other non-transitory digital or analog devices that store data for subsequent retrieval. The data stored by memory 82 can include computer-readable instructions that, when executed by processor 80, cause IMD 12 and processor 80 to perform various functions attributed to IMD 12 and processor 80 herein.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

The various components of IMD 12 are coupled to power source 90. Power source 90 provides electrical power to the various components of IMD 12. In various examples, power source 90 is implemented in various ways. For instance, in some examples, power source 90 can comprise one or more non-rechargeable batteries. In such examples, the non-rechargeable batteries may be capable of holding a charge for several years. Furthermore, in some examples, power source 90 can comprise one or more rechargeable batteries. In such examples, the one or more rechargeable batteries may be inductively charged from an external device on a recurring basis. Furthermore, in some examples, power source 90 includes one or more supercapacitors.

Signal generator 84 comprises circuitry that generates electrical signals. Signal generator 84 is electrically coupled to electrodes 40 via leads 18. In addition, signal generator 84 is electrically coupled to housing electrode 58 via an electrical conductor disposed within housing 60 of IMD 12. Signal generator 84 can be configured to generate and deliver electrical stimulation therapy to heart 16. For example, signal generator 84 may deliver defibrillation shocks to heart 16 via at least two of electrodes 58, 40G, 40H, and 40I. Signal generator 84 may deliver pacing pulses via ring electrodes 40A, 40C, 40E coupled to leads 18A, 18B, and 18C, respectively. Signal generator 84 may also deliver pacing pulses via helical electrodes 40B, 40D, and 40F of leads 18A, 18B, and 18C, respectively.

In various examples, signal generator 84 delivers electrical stimulation therapy to heart 16 in various ways. For example, signal generator 84 can deliver pacing, cardioversion, or defibrillation stimulation to heart 16 in the form of electrical pulses. In another example, signal generator 84 can deliver one or more of these types of electrical stimulation therapy in the form of other signals, such as sine waves, square waves, or other substantially continuous time signals.

Signal generator 84 may include a switch module. Processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Sensing module 86 comprises circuitry that receives electrical signals from electrodes 40 and 58. Sensing module 86 provides the electrical signals or data representative of the electrical signals to processor 80 and/or metric generation module 92. Sensing module 86 may include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86.

Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Memory 82 stores parameters 83 and metric data 85. Parameters 83 include configurable values that affect how IMD 12 performs certain operations. In the example of FIG. 5, parameters 83 include metric parameters 100, metric thresholds 102, an electrode vector parameter 104, and a risk threshold 106. Metric parameters 100 include configurable values that affect which patient metrics metric generation module 92 generates and how metric generation module 92 generates the patient metrics. For example, metric parameters 100 can include values that specify which electrodes or sensors to use in detection of various patient metrics. In another example, metric parameters 100 can include values that specify rates at which particular patient metrics are to be measured. In yet another example, metric parameters 100 can include values that specify how to calibrate particular patient metrics.

Metric thresholds 102 are associated with different patient metrics. For example, one of metric thresholds 102 can be associated with an intrathoracic impedance metric, another one of metric thresholds 102 can be associated with a blood pressure metric, and so on. Each of metric thresholds 102 may include a configurable threshold value. Patient 14 may be at a greater risk of suffering a heart failure decompensation event in the near future if a given patient metric exceeds the metric threshold associated with the given patient metric. For example, patient 14 may be at a greater risk of suffering a heart failure decompensation event in the near future if an intrathoracic impedance metric is greater than 60 ohms. In this example, a metric threshold associated with the intrathoracic impedance metric specifies 60 ohms. In another example, patient 14 may be at a greater risk of suffering a heart failure decompensation event in the near future if a ventricular contraction rate is greater than 90 beats per minute for 24 hours. In this example, a metric threshold associated with a ventricular contraction rate metric specifies 90 beats per minute for 24 hours.

In some examples, multiple metric thresholds 102 can be associated with a single patient metric. For example, a first metric threshold and a second metric threshold can be associated with an intrathoracic impedance metric. In this example, the first metric threshold can specify a value of 60 ohms and the second metric threshold can specify a value of 100 ohms. In this example, patient 14 may be at an even greater risk of suffering a heart failure decompensation event if an intrathoracic impedance metric exceeds the second metric threshold.

Electrode vector parameter 104 specifies one of electrode vectors 70. For example, electrode vector parameter 104 can specify electrode vector 70F and not specify electrode vectors 70A-70E. As described in detail elsewhere in this disclosure, processor 80 uses the electrode vector specified by electrode vector parameter 104 when processor 80 determines the risk that patient 14 will suffer a heart failure decompensation event in the near future.

As described in detail elsewhere in this disclosure, processor 80 uses risk threshold 106 to determine whether the risk of patient 14 suffering a heart failure decompensation event in the near future is sufficiently high that one or more people should be alerted. For example, risk threshold 106 can specify a number. In this example, if the number of exceeded metric thresholds is greater than or equal to the number specified by risk threshold 106, IMD 12 may perform an alert operation to alert one or more people that patient 14 is at a significant risk of suffering a heart failure decompensation event in the near future.

In some examples, processor 80 may change parameters 83 in response to various events. For instance, in some examples, parameters 83 may change automatically in response to patient conditions. For example, processor 80 may adjust one of metric thresholds 102 if patient 14 is experiencing certain arrhythmias or normal electrograms change. Furthermore, in some examples, processor 80 may change one or more of parameters 83 in response to input from a user. For example, telemetry module 88 may receive commands from programmer 24 to modify one or more of parameters 83.

Metric generation module 92 generates metric data 85 and stores metric data 85 in memory 82. Metric data 85 includes patient metrics measured or sensed by IMD 12. In various examples, metric generation module 92 can generate various metric data 85 that provide various types of information about patient 14. For example, metric generation module 92 can generate an electrogram of heart 16. In other examples, metric generation module 92 can generate patient metrics that indicate polarization and depolarization of heart 16, patient metrics that indicate electrical stimulation therapies delivered to patient 14, and other types of information about patient 14.

In the example of FIG. 5, metric generation module 92 includes an impedance module 94. Metric generation module 92 may use impedance module 94 to generate intrathoracic impedance measurements. As described herein, impedance module 94 may utilize any of the electrodes of FIG. 1, 2 or 4 to generate intrathoracic impedance measurements. In other examples, impedance module 94 may utilize separate electrodes coupled to IMD 12 or in wireless communication with telemetry module 88. Once impedance module 94 measures the intrathoracic impedance of patient 14, metric generation module 92 can generate a thoracic fluid index metric by using the impedance measurements to generate thoracic fluid indexes and compare the indexes to the thoracic fluid index threshold defined in metric parameters 83.

Furthermore, in the example of FIG. 5, metric generation module 92 includes an activity sensor 96. Activity sensor 96 may comprise one or more devices capable of detecting activities of patient 14. For example, activity sensor 96 may include accelerometers that are capable of detecting motion and/or position of patient 14. Metric generation module 92 may generate one or more patient metrics based on the magnitude or duration of each activity.

In some examples, metric generation module 92 may generate therapy metrics. Therapy metrics provide information about therapies to patient 14 by IMD 12. For example, metric generation module 92 may monitor signals through signal generator 84 or receive therapy information directly from processor 80 for the detection. Example therapy metrics may include a cardiac resynchronization therapy percentage and an electrical shock event. The cardiac resynchronization therapy percentage may indicate an amount of time each day that patient 14 receives some kind of electrical stimulation therapy to heart 16. This electrical stimulation therapy may come in the form of pacing pulses, cardioversion, and/or defibrillation, for example. Low therapy percentages may indicate that beneficial therapy is not being delivered and that adjustment of therapy parameters, e.g., an atrioventricular delay or a lower pacing rate, may improve therapy efficacy. In one example, higher therapy percentages may indicate that heart 16 is sufficiently pumping blood through the vasculature with the aid of therapy to prevent fluid buildup. In other examples, higher therapy percentages may indicate that heart 16 is unable to keep up with blood flow requirements. An electrical shock may be a defibrillation event or other high energy shock used to return heart 16 to a normal rhythm. Metric generation module 92 may detect these patient metrics as well and compare them to a cardiac resynchronization therapy percentage and shock event threshold, respectively, defined in metric parameters 83 to determine when each patient metric has become critical. In one example, the electrical shock event may become critical if patient 14 even receives one therapeutic shock.

In some examples, metric data 85 may store the data for each metric on a rolling basis and delete old data as necessary or only for a predetermined period of time, e.g., an evaluation window. Processor 80 may access metric data 85 when necessary to retrieve and transmit metric data 85 and/or to determine the risk of patient 14 suffering a heart failure decompensation event.

In various examples, metric generation module 92 can be implemented in various ways. For example, IMD 12 can provide the functionality of metric generation module 92 when processor 80 or other logic circuits execute particular software or firmware instructions. In other examples, IMD 12 can provide one or more dedicated logic circuits, such as ASICs, that provide the functionality of metric generation module 92.

Figure 6:
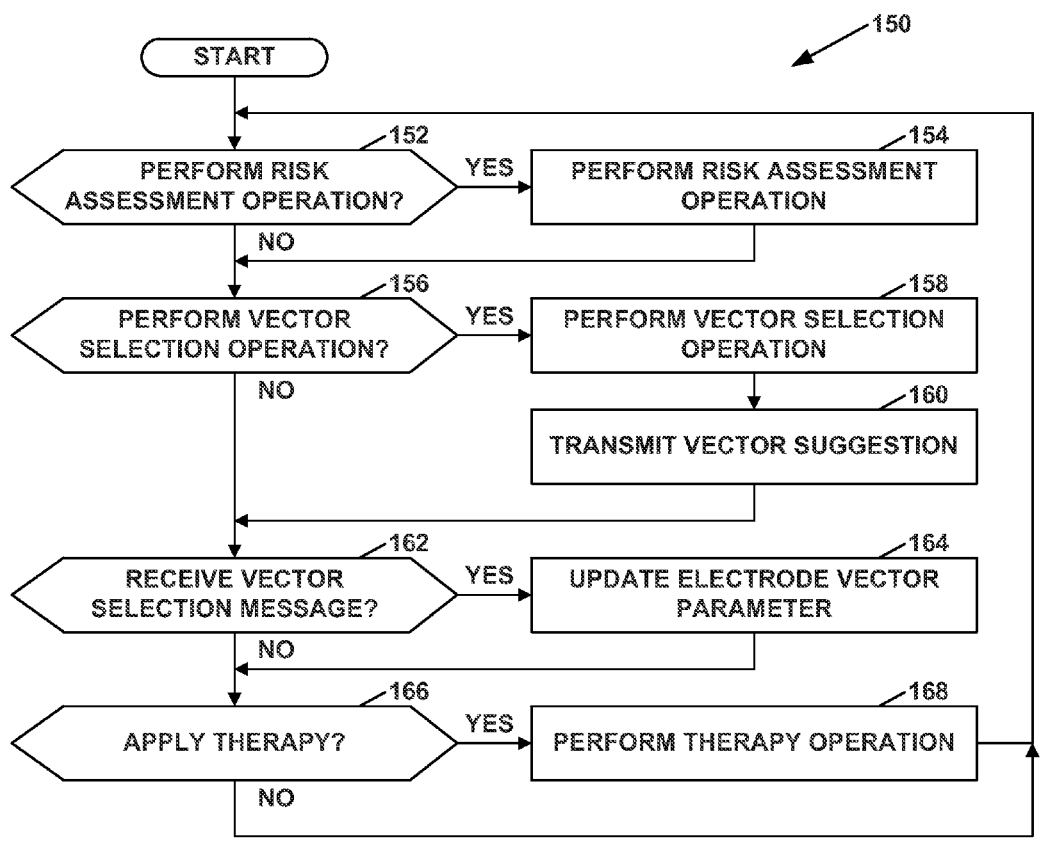
FIG. 6 is a flowchart that illustrates an example runtime operation performed by a processor of the IMD.

Processor 80 performs a runtime operation to control activities of IMD 12. Processor 80 can continue performing the runtime operation during normal operation of IMD 12. In various examples, processor 80 performs various runtime operations. FIG. 6, described in detail below, is a flowchart that illustrates an example runtime operation. Readers will understand that processor 80 may perform runtime operations different than the example runtime operation illustrated in FIG. 6.

When processor 80 performs the runtime operation, processor 80 can read metric data 85 from memory 82 on a recurring basis. Processor 80 uses metric data 85 to perform a risk assessment operation in order to determine a risk that patient 14 will experience a heart failure decompensation event in the near future. Processor 80 can perform this risk assessment operation on a recurring basis.

As discussed above, IMD 12 can generate impedance measurements using one or more of electrode vectors 70. When processor 80 performs the runtime operation, processor 80 can use metric data 85, such as intrathoracic impedance measurements, to perform a vector selection operation in order to select one of electrode vectors 70. Subsequently, when processor 80 performs the risk assessment operation again, processor 80 can determine the risk of a heart failure decompensation event in the near future based on the impedance measurements generated by the selected electrode vector, and not based on impedance measurements generated by other ones of electrode vectors 70.

FIG. 6 is a flowchart that illustrates an example runtime operation 150 performed by processor 80. After processor 80 starts runtime operation 150, processor 80 determines whether to perform a risk assessment operation (152). If the processor 80 makes the determination to perform the risk assessment operation ("YES" of 152), processor 80 performs the risk assessment operation (154). When processor 80 performs the risk assessment operation, processor 80 determines a risk that patient 14 will suffer a heart failure decompensation event in the near future. Processor 80 can determine the risk based at least in part on intrathoracic impedance measurements.

In various examples, processor 80 determines whether to perform a risk assessment operation in various ways. For example, processor 80 may make the determination to perform the risk assessment operation when a recurrence period has expired. In this example, the recurrence period can have various durations, such as one minute, five minutes, ten minutes, one hour, one day, or periods of time having other durations. In another example, processor 80 may make the determination to perform the risk assessment operation whenever one or more events occur. In this example, such events can include a patient metric rising above a given threshold, receipt of a request from programmer 24 for a risk score, and other events.

In various examples, processor 80 performs various risk assessment operations. FIG. 6, described in detail below, illustrates an example risk assessment operation. Readers will understand that processor 80 can perform risk assessment operations other than the example risk assessment operation illustrated in FIG. 6. For example, processor 80 can perform a risk assessment operation based solely on intrathoracic impedance values instead of on a plurality of patient metrics. Furthermore, in some examples, when processor 80 performs the risk assessment operation, processor 80 may not determine the risk based on impedance measurements generated using ones of the electrode vectors that were not selected during the most recent performance of a vector selection operation.

After processor 80 performs the risk assessment operation or after processor 80 makes the determination not to perform the risk assessment operation ("NO" of 152), processor 80 determines whether to perform a vector selection operation (156). If processor 80 makes the determination to perform the vector selection operation ("YES" of 156), processor 80 performs the vector selection operation (158). When processor 80 performs the vector selection operation, processor 80 selects a given electrode vector from among electrode vectors 70. Impedance measurements generated using the selected electrode vector may be more reliable than impedance measurements generated using other ones of electrode vectors 70 for determining the likelihood that patient 14 will experience a heart failure decompensation event in the near future.

In various examples, processor 80 makes the determination whether to perform the vector selection operation in various ways. For example, processor 80 may make the determination to perform the vector selection operation whenever a recurrence period has expired. In this example, the recurrence period can have various durations, such as five minutes, one hour, one day, one week, one month, or periods of time having other durations. In some examples, the recurrence period can change in response to various conditions. For example, if patient 14 is exercising, the recurrence period can be shorter, e.g., one minute, than when patient 14 is not exercising, e.g., one hour. In examples where processor 80 uses a recurrence period to determine whether to perform the risk assessment operation, the recurrence period used to determine whether to perform the vector selection operation may be the same or different than the recurrence period used to determine whether to perform the risk assessment operation.

In another example, processor 80 may make the determination to perform the vector selection operation in response to other events. For example, processor 80 may make the determination to perform the vector selection operation in response to detecting that the electrode vector indicated by electrode vector parameter 104 has generated one or more impedance measurements that lie outside an expected range. In another example, processor 80 may make the determination to perform the vector selection operation in response to detecting that the signal-to-noise ratio of the electrode vector indicated by electrode vector parameter 104 has risen above a certain threshold or has risen by a particular percentage. In yet another example, processor 80 may use metric data 85 to determine whether an activity level of patient 14 has dropped by a particular amount, e.g. by 30%. In this example, processor 80 may make the determination to perform the vector selection operation in response to detecting that that the activity level of patient 14 has dropped by the particular amount. In yet another example, processor 80 may use metric data 85 to determine a heart rate variability of patient 14. In this example, processor 80 may make the determination to perform the vector selection operation in response to a change in the heart rate variability of patient 14. In yet another example, processor 80 may make the determination to perform the vector selection operation based on a time of day. Thus, processor 80 may make the determination to perform the vector selection operation in the evening and again in the morning.

In various examples, processor 80 may perform various vector selection operations. For example, FIGS. 7 and 8, described in detail below, illustrate different example vector selection operations. Readers will understand that processor 80 can perform vector selection operations other than example vector selection operations illustrated in FIGS. 7 and 8.

In the example of FIG. 6, processor 80 transmits a vector suggestion message to programmer 24 after performing the vector selection operation (160). The vector suggestion message indicates the electrode vector selected during the vector selection operation.

After sending the vector suggestion message to programmer 24 or after making the determination not to perform the vector selection operation ("NO" of 156), processor 80 determines whether IMD 12 has received a vector selection message from programmer 24 (162). The vector selection message indicates an electrode vector whose intrathoracic impedance measurements are to be used during the risk assessment operation. If IMD 12 has received the vector selection message from programmer 24 ("YES" if 162), processor 80 updates electrode vector parameter 104 to specify the electrode vector indicated by the vector selection message (164). As discussed above, processor 80 uses intrathoracic impedance measurements of the electrode vector indicated by electrode vector parameter 104 when performing the risk assessment operation. In the example of FIG. 6, processor 80 does not update electrode vector parameter 104 if processor 80 does not receive the vector selection message. Hence, processor 80 can continue using intrathoracic impedance measurements from the same electrode vector, despite the vector selection operation potentially selecting a different electrode vector.

After updating electrode vector parameter 104 or after determining that IMD 12 has not received a vector selection message from programmer 24 ("NO" of 162), processor 80 determines whether to apply a therapy to heart 16 (166). If processor 80 makes the determination to apply the therapy to heart 16 ("YES" of 166), processor 80 performs a therapy operation that causes IMD 12 to apply the therapy to heart 16 (168).

In various examples, processor 80 determines whether to apply a therapy to heart 16 in various ways. Furthermore, in various examples, processor 80 performs various therapy operations to apply various therapies to heart 16. For example, processor 80 may perform a therapy operation in which processor 80 controls signal generator 84 to deliver electrical stimulation therapies to heart 16. In this example, processor 80 can execute one or more therapy programs stored in memory 82. Execution of different therapy programs by processor 80 causes processor 80 to control signal generator 84 to deliver different electrical stimulation therapies to heart 16. For example, processor 80 may control signal generator 84 to deliver electrical pulses with the amplitudes, pulse widths, frequency, or electrode polarities specified by therapy programs.

In another one example, processor 80 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Processor 80 may also analyze electrograms in conjunction with a real-time clock to determine a nighttime heart rate or a daytime heart rate or a difference between the day and night heart rate, and also analyze electrograms to determine a heart rate variability, or any other detectable cardiac events from one or more electrograms. If processor 80 detects an atrial fibrillation or atrial tachycardia, processor 80 can perform an anti-fibrillation or anti-tachycardia operation to stop the fibrillation or tachycardia. In other examples, IMD 12 may deliver pacing therapy to try and reduce heart failure symptoms.

In yet another example, processor 80 can perform a therapy operation in which processor 80 automatically provides a therapy to patient 14 based on the risk of patient 14 experiencing a heart failure decompensation event and/or based on one of the patient metrics. For example, if processor 80 determines that the risk of a heart failure decompensation event is sufficiently high, processor 80 can activate a drug pump that delivers a dose of medication, e.g., nitroglycerin, to reduce the risk of the heart failure decompensation event.

After performing the therapy operation or after making the determination not to perform the therapy operation ("NO" of 166), processor 80 can perform runtime operation 150 again. Processor 80 can continue performing runtime operation 150 until an event occurs that instructs processor 80 to stop performing runtime operation 150. For example, processor 80 can continue performing runtime operation 150 until IMD 12 receives instructions from programmer 24 to stop performing runtime operation 150. In this way, IMD 12 performs the risk assessment operation on a first recurring basis and performs the vector selection operation on a second recurring basis.

Readers will understand that processor 80 can perform operations other than runtime operation 150. For example, when processor 80 performs another operation, processor 80 may update electrode vector parameter 104 to indicate the electrode vector identified during the vector selection operation automatically without first waiting to receive a vector selection message from programmer 24. In another example, processor 80 can perform a runtime operation that does not perform a therapy operation. In yet another example, processor 80 can perform a runtime operation in which two or more of the steps of runtime operation 150 are performed concurrently, rather than sequentially.

In yet another example, processor 80 can perform a runtime operation in which IMD 12 does not perform the risk assessment operation. For example, processor 80 can perform a runtime operation in which an external computing device, e.g., programmer 24, performs a risk assessment operation to determine a risk that patient 14 will experience a heart failure decompensation event in the near future. In this example, processor 80 may still collect and store the data for each patient metric or organize and format the patient metric data before transmitting the patient metrics in metric data 85 to the external computing device. Furthermore, in this example, processor 80 may transmit the metric thresholds with the patient metrics so that the external computing device may determine the risk of patient 14 suffering a heart failure decompensation event.

In some examples, runtime operation 150 is a method for determining a risk of a patient suffering a heart failure decompensation event in the near future. This method can comprise using, by a medical device implanted in the patient, a plurality of electrode vectors to generate a plurality of intrathoracic impedance measurements, each of the electrode vectors being a different combination of electrodes. The method also comprises performing, by the medical device, a vector selection operation on a first recurring basis. Each time the medical device performs the vector selection operation, the medical device selects a given electrode vector from among the plurality of electrode vectors, the intrathoracic impedance measurements generated using the given electrode vector being at a current time likely to be more reliable than the intrathoracic impedance measurements generated using other ones of the electrode vectors for determining the risk. The method also comprises performing, by the medical device, a risk assessment operation on a second recurring basis. Each time the medical device performs the risk assessment operation, the medical device determines the risk based at least in part on intrathoracic impedance measurements generated using one of the electrode vectors that was selected during a most recent performance of the vector selection operation.

Figure 7:
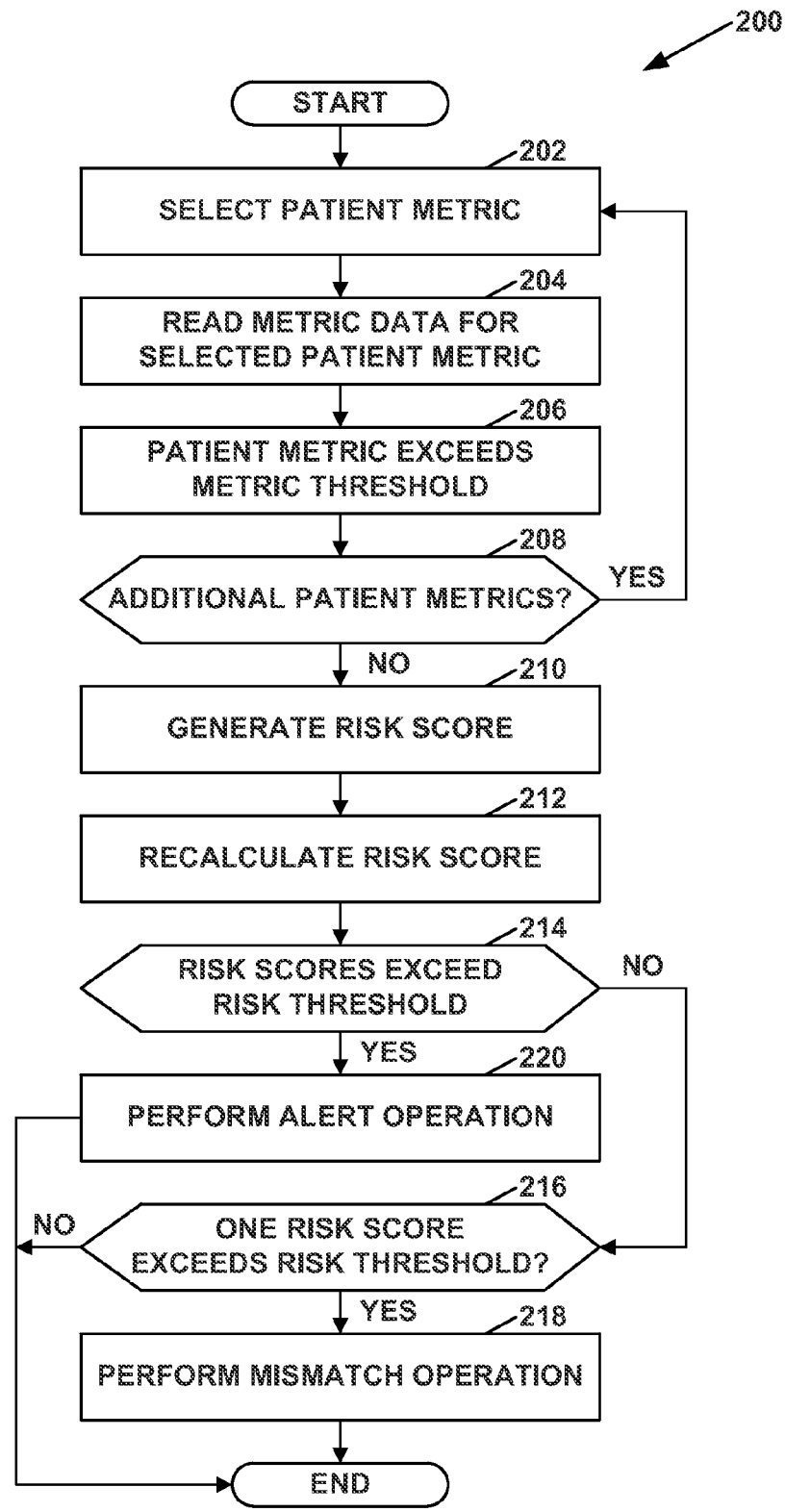
FIG. 7 is a flowchart that illustrates an example risk assessment operation.

FIG. 7 is a flowchart that illustrates an example risk assessment operation 200. After processor 80 starts performing risk assessment operation 200, processor 80 selects a patient metric from among a plurality of applicable patient metrics (202). For ease of explanation, this disclosure refers to the selected one of the patient metrics as the selected patient metric. As discussed above, metric generation module 92 can generate a plurality of patient metrics. The applicable patient metrics may be a subset of the patient metrics generated by metric generation module 92. In some examples, a user may use programmer 24 to select the set of applicable patient metrics.

In various examples, processor 80 can select the patient metric from among the plurality of applicable patient metrics in various ways. For example, each of the patient metrics can have a rank. In this example, processor 80 selects higher-ranked patient metrics before selecting lower-ranked patient metrics. In another example, processor 80 selects the patient metrics according to an order in which data related to the patient metrics are stored in memory 82.

Processor 80 then reads metric data 85 for the selected patient metric from memory 82 (204). For example, if the selected patient metric is a thoracic fluid index, processor 80 can read metric data 85 from memory 82 that indicate the thoracic fluid index.

Next, processor 80 determines whether the selected patent metric exceeds its corresponding metric threshold (206). For example, if the selected patient metric is a thoracic fluid index, processor 80 can determine whether the thoracic fluid index is above or below a particular threshold. In another example, if the selected patient metric is an intrathoracic impedance measurement, processor 80 can determine whether the intrathoracic impedance measurement is above or below a particular threshold.

In some examples, exceeding a metric threshold does not require the detected value of the patient metric to be greater than the magnitude of the threshold. For some patient metrics, exceeding the metric threshold may occur when the value of the patient metric is less than the metric threshold. Therefore, a metric threshold can be a boundary that triggers the metric's inclusion in the heart failure risk score.

After determining whether the selected patient metric exceeds the associated metric threshold, processor 80 determines whether there are additional patient metrics (208). If there are additional patient metrics ("YES" of 208), processor 80 selects another one of the patient metrics (202). Processor 80 can continue performing steps 202, 204, 206, and 208 until there are no additional patient metrics.

If there are no additional patient metrics ("NO" of 208), processor 80 generates a risk score (210). The value of the risk score can be correlated with a likelihood that patient 14 will experience a heart failure decompensation event in the near future. For example, as it becomes more likely that patient 14 will experience a heart failure decompensation event in the near future, the risk score may increase.

In various examples, processor 80 generates the risk score in various ways. For example, processor 80 can generate the risk score by dividing the number of exceeded metric thresholds by the total number of applicable metric thresholds. The applicable metric thresholds are metric thresholds that are applicable to the applicable patient metrics. For instance, if there are eight metric thresholds and two of the metric thresholds are exceeded by their corresponding patient metrics, processor 80 may generate the risk score as 0.25, i.e., ⅖. In another example, the risk score may be a non-numerical score, such as a level, e.g., high, medium, or low risk of heart failure.

In yet another example, weights are assigned to one or more of the metric thresholds. In this example, processor 80 may calculate the risk score as a sum or a multiplication product of the weights of the exceeded metric thresholds. In this way, some patient metrics may have greater impact on the risk score than other patient metrics. For instance, a metric threshold associated with an intrathoracic impedance metric may be weighted such that the intrathoracic impedance metric has twice the impact of other patient metrics).

After calculating the risk score, processor 80 can recalculate the risk score (214). In some circumstances, the intrathoracic impedance measurements generated using the selected electrode vector (i.e., the electrode vector indicated by electrode vector parameter 104) may be inaccurate. For example, if the selected electrode vector includes an electrode on a broken lead, the intrathoracic impedance measurements generated using the selected electrode may be inaccurate. Inaccurate intrathoracic impedance measurements can cause the risk score to exceed risk threshold 106 even though patient 14 is not actually at a high risk of experiencing a heart failure decompensation event in the near future. Moreover, inaccurate intrathoracic measurements can cause the risk score to be below risk threshold 106 even though patient 14 is actually at a high risk of experiencing a heart failure decompensation event in the near future. When processor 80 recalculates the risk score, processor 80 uses one or more intrathoracic impedance measurements generated using electrode vectors other than the selected electrode vector. In this way, processor 80 may use intrathoracic impedance measurements generated using another one of the electrode vectors to confirm the risk of patient 14 suffering a heart failure decompensation event in the near future.

After recalculating the risk score, processor 80 determines whether both of the risk scores exceed risk threshold 106 (214). In various examples, risk threshold 106 may have various values. For example, processor 80 can calculate the risk score by determining the total number of applicable patient metrics that exceed their associated thresholds. In this example, risk threshold 106 can be set to an integer number, such as two, three, or another number. Thus, in this example, if the number of exceeded metric thresholds is greater than the number indicated by risk threshold 106, processor 80 determines that the risk score exceeds risk threshold 106. In another example, processor 80 can calculate the risk score as a percentage of the applicable metric thresholds that are exceed by their associated patient metrics. In this example, risk threshold 106 can be a predetermined percentage, such as 10%, 25%, or another percentage. In some examples, risk threshold 106 may have different values for patients of differing age, weight, cardiac condition, or any number of other risk factors. In some examples, a user may use programmer 24 to set risk threshold 106.

If both the risk scores do not exceed risk threshold 106 ("NO" of 214), processor 80 may determine whether one of the risk scores exceeds risk threshold 106 (216). This situation can occur when the original risk score exceeds risk threshold 106, but the recalculated risk score does not, and vice versa. Consequently, if one of the risk scores exceeds risk threshold 106 ("YES" of 216), processor 80 can perform a mismatch operation (218). In various examples, processor 80 can perform various actions during the mismatch operation. For example, processor 80 can perform a vector selection operation to select a new electrode vector. Furthermore, in some examples, processor 80 can cause telemetry module 88 to transmit one or more alert messages to programmer 24.

However, if both of the risk scores are below risk threshold 106, patient 14 may be unlikely to experience a heart failure decompensation event in the near future. Hence, if the both of the risk score do not exceed risk threshold 106 ("NO" of 216), processor 80 ends risk assessment operation 200.

On the other hand, if both of the risk scores exceed risk threshold 106, there is a significant risk that patient 14 will experience a heart failure decompensation event in the near future. Accordingly, if both of the risk scores exceed risk threshold 106 ("YES" of 214), processor 80 can perform an alert operation (220). The alert operation can alert one or more people that there is a significant risk that patient 14 will experience a heart failure decompensation event in the near future. In various examples, processor 80 can perform various alert operations. For instance, in some alert operations, processor 80 provides an alert to a user of an external computing device, such as programmer 24. In this instance, the alert may include data from patient metrics and/or the heart failure risk score. Furthermore, in some alert operations, processor 80 provides an alert with the heart failure risk score at a time that programmer 24 or another device initiates communication with IMD 12. In other example alert operations, processor 80 uses telemetry module 88 to push an alert to programmer 24 or another computing device.

Furthermore, in some alert operations, IMD 12 directly indicates to patient 14 that medical treatment is needed due to the increased risk that patient 14 will suffer a heart failure decompensation event in the near future. In examples in which processor 80 performs such alert operations, IMD 12 may include a speaker to emit an audible sound through the skin of patient 14 or a vibration module that vibrates to notify patient 14 that medical attention is needed. In some examples, processor 80 may directly alert patient 14 if IMD 12 cannot send the alert to an external computing device because no connection to the external computing device is available.

In some alert operations, IMD 12 may signal programmer 24 to further communicate with and pass the alert through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., patient metric data or heart failure risk score, to the user.

Figure 8:
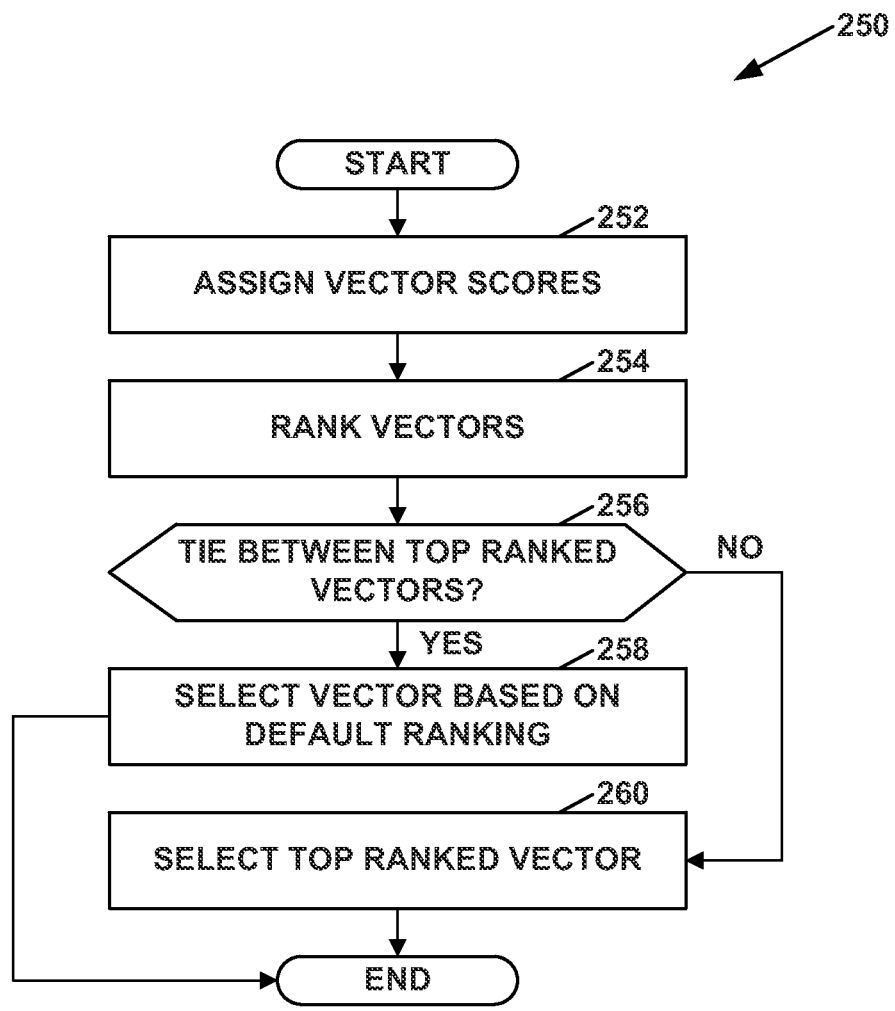
FIG. 8 is a flowchart that illustrates a first example vector selection operation.

FIG. 8 is a flowchart that illustrates an example vector selection operation 250. After processor 80 starts performing vector selection operation 250, processor 80 assigns vector scores to electrode vectors 70 (252). Processor 80 can use intrathoracic impedance measurements previously generated using electrode vectors 70 to assign vector scores to electrode vectors 70. In various examples, processor 80 assigns vector scores to electrode vectors 70 in various ways. For example, electrode vectors 70 can have a plurality of characteristics. The characteristics of an electrode vector can, for example, include a signal-to-noise ratio being above certain thresholds, impedance measurements generated by the electrode vector being within a certain number of standard deviations from an expected value, tendency for intrathoracic impedance measurements generated by the electrode vector to vary from measurement-to-measurement, tendency for changes in intrathoracic impedance measurements generated by the electrode vector to align with changes in intrathoracic impedance measurements generated by other electrode vectors, tendency for intrathoracic impedance measurements generated by the electrode vector to indicate increased risk of heart failure event when other patient metrics indicate increased risk of a heart failure event, and so on. In this example, each of the characteristics is associated with a point value. In this example, if a given electrode vector has a given characteristic, processor 80 adds the point value associated with the given characteristic to a score for the given electrode vector.

Processor 80 then ranks electrode vectors 70 based on the vector scores (254). For example, processor 80 can rank an electrode vector having a high vector score higher than electrode vectors having lower vector scores. After ranking electrode vectors 70, processor 80 determines whether there is a tie between top ranked electrode vectors (256). For instance, two of electrode vectors 70 can have the same given vector score and none of the other ones of electrode vectors 70 have vector scores higher than the given vector score.

If there is a tie between the top-ranked electrode vectors ("YES" of 256), processor 80 selects one of the top-ranked electrode vectors based at least in part on a default ranking of electrode vectors 70 (258). Processor 80 can then end vector selection operation 250. The default ranking of electrode vectors 70 can be pre-configured into IMD 12. For example, the default ranking of electrode vectors 70 can be pre-configured into IMD 12 such that electrode vector 70B has a highest ranking, followed by electrode vector 70A, and so on.

In some examples, the default ranking of electrode vectors 70 can be altered by a user through programmer 24. The default ranking of electrode vectors 70 can be based on the experience of the user of programmer 24. Furthermore, in some examples, processor 80 can perform an operation that establishes the default ranking based on past performance of electrode vectors 70.

Otherwise, if there is no tie between the top-ranked electrode vectors ("NO" of 256), processor 80 selects the top-ranked electrode vector (260). After selecting the top-ranked electrode vector, processor 80 ends vector selection operation 250.

Figure 9:
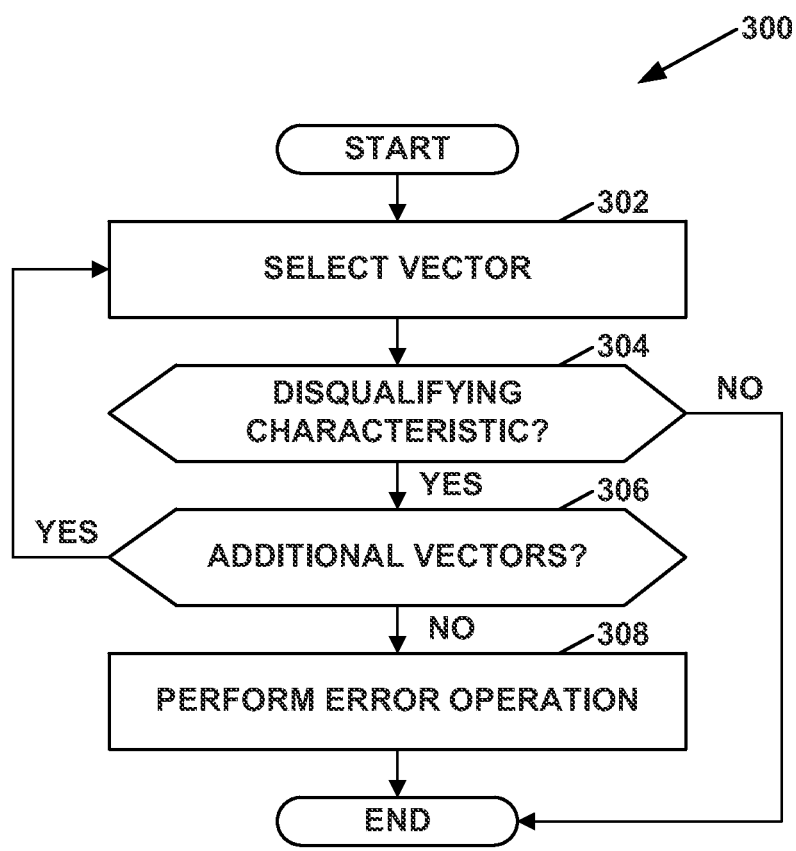
FIG. 9 is a flowchart that illustrates a second example vector selection operation.

FIG. 9 is a flowchart that illustrates a second example vector selection operation 300. After processor 80 starts performing vector selection operation 300, processor 80 selects an electrode vector (302). In various examples, processor 80 selects the electrode vector in various ways. For example, parameters 83 can specify a default ranking of electrode vectors 70. The default ranking can be based on experience of a user of programmer 24. In this example, processor 80 can select the highest-ranked electrode vector in the default ranking that has not previously been selected during performance of vector selection operation 300. In this example, impedance measurements of electrode vectors that are high in the default ranking may historically be more reliable than impedance measurements generating using lower ranked vectors for determining the likelihood that patient will experience a heart failure event in the near future.

After selecting the electrode vector, processor 80 determines whether the selected electrode vector has one or more disqualifying characteristics (304). Processor 80 can use intrathoracic impedance measurements previously generated using electrode vectors 70 to determine whether the selected electrode vector has one or more disqualifying characteristics. In various examples, processor 80 can determine whether the selected electrode vector has various disqualifying characteristics. For example, parameters 83 can include a list of "blacklisted" electrode vectors. A user can use programmer 24 to configure the list of blacklisted electrode vectors. The user can add one of electrode vectors to the list of blacklisted electrode vectors for various reasons. For instance, the user can add a given electrode vector to the list of blacklisted electrode vectors if the given electrode vector includes an electrode of a malfunctioning or broken lead. In this example, processor 80 can determine that the selected electrode vector has a disqualifying characteristic when the selected electrode vector is among the "blacklisted" electrode vectors. In another example, processor 80 can determine that the selected electrode vector has a disqualifying characteristic if the impedance measurements generated using the selected electrode vectors are outside a particular range. In yet another example, processor 80 can determine that the selected electrode vector has a disqualifying characteristic if the selected electrode vector has a signal-to-noise ratio that is below a given threshold.

If the selected electrode vector does not have any disqualifying characteristics ("NO" of 304), processor 80 keeps the selected electrode vector and vector selection operation 300 ends. Otherwise, if the selected electrode vector has one or more disqualifying characteristics ("YES" of 304), processor 80 determines whether there are one or more additional electrode vectors that have not yet been selected during the performance of vector selection operation 300 (306).

If processor 80 determines that there no additional electrode vectors ("NO" of 306), processor 80 performs an error operation (308). In various examples, processor 80 can perform various error operations. For example, processor 80 can perform an error operation in which processor 80 sends an alert to programmer 24. In another example, processor 80 can perform an error operation in which IMD 12 alerts patient 14 directly. Processor 80 may end vector selection operation 300 after performing the error operation.

However, if there are one or more electrode vectors ("YES" of 306), processor 80 can select another one or electrode vectors (302). Processor 80 can then perform steps 304, 306, and/or 308 with regard to this electrode vector. In this way, processor 80 can select one of electrode vectors 70 that does not have a disqualifying characteristic or can determine that none of the electrode vectors 70 are suitable.

Figure 10:
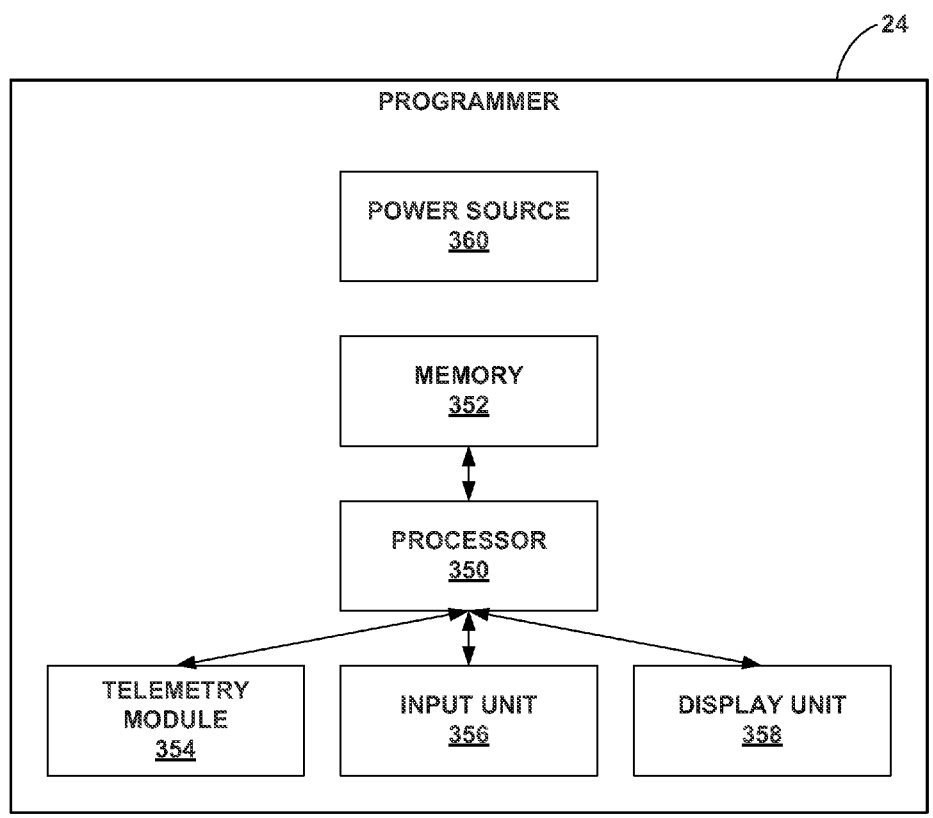
FIG. 10 is a functional block diagram that illustrates an example configuration of a programmer.

FIG. 10 is a functional block diagram that illustrates an example configuration of external programmer 24. As shown in the example of FIG. 9, programmer 24 may include a processor 350, a memory 352, a telemetry module 354, an input unit 356, a display unit 358, and a power source 360. Programmer 24 may be a dedicated hardware device with dedicated software for programming of IMD 12.

Alternatively, programmer 24 may be an off-the-shelf computing device running an application that enables programmer 24 to program IMD 12.

Processor 350 can cause display unit 358 to display one or more user interfaces to the user. In some examples, display unit 358 is a touchscreen. Although the example of FIG. 9 shows display unit 358 as being within programmer 24, display unit 358 can, in some examples, be outside a housing of programmer 24. For instance, display unit 358 can be a separate monitor or display screen.

The user may use input unit 356 to provide input to programmer 24. In various examples, programmer 24 can include various types of input devices. For example, input unit 356 can include a keyboard, a touch-sensitive surface, a pointing device, a microphone, or another mechanism for receiving input from a user.

Processor 350 can take the form one or more microprocessors, DSPs, ASICs, FPGAs, programmable logic circuitry, or the like, and the functions attributed to processor 350 herein may be embodied as hardware, firmware, software or any combination thereof. Memory 352 may store instructions that cause processor 350 to provide the functionality ascribed to programmer 24 herein, and information used by processor 350 to provide the functionality ascribed to programmer 24 herein. Memory 352 may include any fixed or removable magnetic, optical, or electrical media, such as RAM, ROM, CD-ROM, hard or floppy magnetic disks, EEPROM, or the like. Memory 352 may also include a removable memory portion that may be used to provide memory updates or increases in memory capacities. A removable memory may also allow patient data to be easily transferred to another computing device, or to be removed before programmer 24 is used to program therapy for another patient.

Programmer 24 can use telemetry module 354 to may communicate wirelessly with IMD 12. In various examples, programmer 24 can communicate wirelessly with IMD 12 in various ways. For example, programmer 24 can use technologies such as using RF communication or proximal inductive interaction to wirelessly communicate with IMD 12. This wireless communication is possible through the use of telemetry module 354, which may be coupled to an internal antenna or an external antenna. An external antenna that is coupled to programmer 24 may correspond to the programming head that may be placed over heart 16, as described above with reference to FIG. 1. Telemetry module 354 may be similar to telemetry module 88 of IMD 12 (FIG. 5).

In this manner, telemetry module 354 may receive an alert or notification of the heart failure risk score from telemetry module 88 of IMD 12. The alert may be automatically transmitted, or pushed, by IMD 12 when the heart failure risk score becomes critical. In addition, the alert may comprise a notification to a healthcare professional, e.g., a clinician or nurse, of the risk score and/or an instruction to patient 14 to seek medical treatment for the potential heart failure condition. In response to receiving the alert, processor 350 can cause display unit 358 to present the alert to the healthcare professional regarding the risk score or present an instruction to patient 14 to seek medical treatment.

Either in response to pushed heart failure information, e.g., the risk score or patient metrics, or requested heart failure information, processor 350 can cause display unit 358 to present the patient metrics and/or the heart failure risk score to the user. In some examples, processor 350 can cause display unit 358 to highlight each of the patient metrics that have exceeded the respective one of the plurality of metric specific thresholds. In this manner, the user may quickly review those patient metrics that have contributed to a critical heart failure risk score.

Upon receiving the alert, the user may provide input to programmer 24 via input unit 356 to cancel the alert, forward the alert, retrieve data regarding the heart failure risk score (e.g., patient metric data), modify the metric specific thresholds used to determine the risk score, or conduct any other action related to the treatment of patient 14. In some examples, the user may be able to review raw data to diagnose any other problems with patient 14. In some examples, processor 350 can cause display unit 358 to display information that suggests treatment along with the alert, e.g., certain drugs and doses, to minimize symptoms and tissue damage that could result from heart failure. User interfaces displayed on display unit 358 may also allow the user to specify the type and timing of alerts based upon the severity or criticality of the heart failure risk score. In addition to the heart failure risk score, user interfaces displayed on display unit 358 may also provide the underlying parameters to allow the user to monitor therapy efficacy and remaining patient conditions.

In some examples, processor 350 of programmer 24 and/or one or more processors of one or more networked computers may perform all or a portion of the techniques described herein with respect to processor 80 and IMD 12. For example, processor 350 or a metric detection module within programmer 24 may analyze patient metrics to detect those metrics exceeding thresholds and to generate the heart failure risk score. Furthermore, in some examples, processor 350 can perform a vector selection operation or a risk assessment operation.

Figure 11:
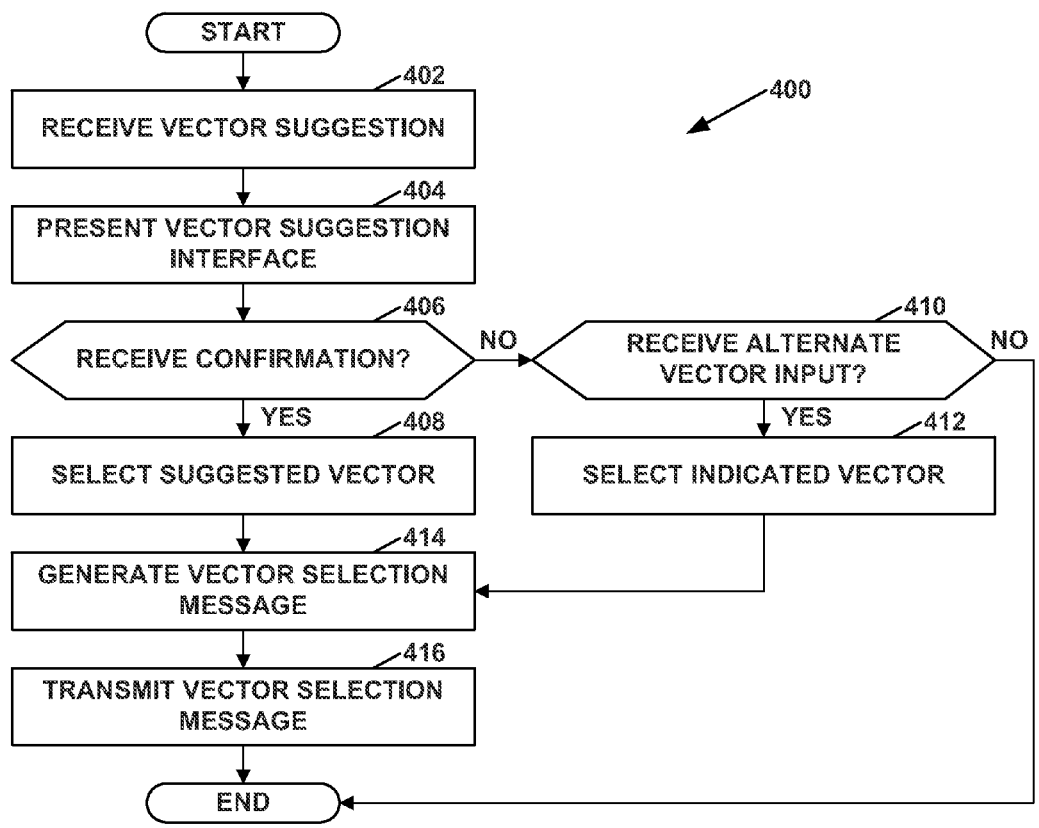
FIG. 11 is a flowchart that illustrates an example operation performed by the programmer.

FIG. 11 is a flowchart that illustrates an example operation 400 performed by programmer 24. After programmer 24 starts performing operation 400, telemetry module 354 receives a vector suggestion message from IMD 12 (402). After, or in response to, receiving the vector suggestion message, processor 350 causes display unit 358 to present a vector suggestion interface (404). The vector suggestion interface specifies the suggested electrode vector. The vector suggestion interface also includes one or more user interface controls that enable the user of programmer 24 to confirm whether IMD 12 should use the suggested electrode vector to determine whether patient 14 is likely to suffer a heart failure event in the near future. Example types of user interface controls include touchscreen buttons, soft buttons, menus elements, checkboxes, and other types of onscreen features that enable users to provide input to programmer 24.

Subsequently, processor 350 determines whether programmer 24 has received suggestion confirmation input (406). In various examples, programmer 24 can receive the suggestion confirmation input in various ways. For example, programmer 24 can have a physical button. In this example, programmer 24 can receive the suggestion confirmation input when the user pushes the physical button. In another example, programmer 24 can display a user interface control on display unit 358. In this example, programmer 24 can receive the suggestion confirmation input when the user selects the user interface control.

If processor 350 has received suggestion confirmation input ("YES" of 406), processor 350 selects the suggested electrode vector (408). Otherwise, if programmer 24 does not receive suggestion confirmation input ("NO" of 406), processor 350 determines whether programmer 24 has received alternate vector input from the user (410). Alternate vector input can indicate one or more electrode vectors other than the suggested electrode vector. If programmer 24 has received alternate vector input from the user ("YES" of 410), processor 350 selects the electrode vector indicated by the alternate vector input (412). Otherwise, if programmer 24 has not received alternate vector input ("NO" of 410), programmer 24 ends operation 400.

After selecting an electrode vector in steps 408 or 412, processor 350 generates a vector selection message (414). The vector selection message indicates the electrode vector selected in steps 408 or 412. After generating the vector selection message, processor 350 causes telemetry module 354 to send the vector selection message to IMD 12 (416). In this way, the user of programmer 24 can decide whether to allow IMD 12 to use the suggested electrode vector or can instruct IMD 12 to use an electrode vector other than the suggested electrode vector.

Various examples have been described. These and other examples are within the scope of the following claims.

What is claimed is:

1. A method for determining a risk of a patient experiencing a heart failure decompensation event in the near future, the method comprising:
   storing, by a medical device implanted in the patient, an electrode vector parameter indicating an electrode vector of a plurality of electrode vectors, each of the electrode vectors being a different combination of electrodes;
   using, by the medical device, a plurality of electrode vectors to generate a plurality of intrathoracic impedance measurements;
   performing, by the medical device, a vector selection operation on a first recurring basis, wherein each time the medical device performs the vector selection operation, the medical device:
      selects a given electrode vector from among the plurality of electrode vectors, the intrathoracic impedance measurements generated using the given electrode vector being at a current time likely to be more reliable than the intrathoracic impedance measurements generated using other ones of the electrode vectors for determining the risk of the patient experiencing the heart failure decompensation event in the near future;
      causes a telemetry unit of the medical device to transmit a vector suggestion message to a programmer after the selection of the given electrode vector, the vector suggestion message specifying the selected electrode vector;
      receives a selection message from the programmer in response to the vector suggestion message, the selection message specifying the selected electrode vector or another one of the electrode vectors; and
      responsive to the selection message, updates the electrode vector parameter to indicate the electrode vector specified by the selection message;
   performing, by the medical device, a risk assessment operation on a second recurring basis, wherein each time the medical device performs the risk assessment operation, the medical device determines the risk based at least in part on intrathoracic impedance measurements generated using the electrode vector indicated by the electrode vector parameter;
   calculating, based on the intrathoracic impedance measurements generated using the electrode vector indicated by the electrode vector parameter, an initial risk score during the risk assessment operation, the risk score being correlated with a likelihood of the patient experiencing the heart failure decompensation event in the near future;
   recalculating the risk score using one or more intrathoracic impedance measurements generated using electrode vectors other than the electrode vector indicated by the electrode vector parameter; and
   responsive to determining that one of, but not both of, the initial risk score and the recalculated risk score exceeds a predetermined risk threshold, performing the vector selection operation.

2. The method of claim 1, wherein performing the vector selection operation comprises:
   assigning vector scores to the electrode vectors; and
   ranking the electrode vectors based on the vector scores assigned to the electrode vectors,
   wherein the medical device selects the given electrode vector when the given electrode vector is a highest-ranked electrode vector.

3. The method of claim 2, wherein assigning vector scores to the electrode vectors comprises: assigning the vector scores to the electrode vectors based at least in part on signal-to-noise ratios of the electrode vectors.

4. The method of claim 2, wherein performing the vector selection operation further comprises:
   determining whether there is a tie among top-ranked ones of the electrode vectors; and
   after determining that there is a tie among the top-ranked electrode vectors, selecting one of the top-ranked electrode vectors based at least in part on a default ranking of the electrode vectors.

5. The method of claim 1, wherein performing the vector selection operation comprises:
   selecting a first electrode vector from among the plurality of electrode vectors;
   after selecting the first electrode vector, determining whether the first electrode vector has one or more disqualifying characteristics; and
   selecting a second electrode vector from among the plurality of electrode vectors after determining that the first electrode vector has one or more disqualifying characteristics.

6. The method of claim 1, wherein performing the vector selection operation on a first recurring basis comprises performing the vector selection operation whenever a recurrence period has expired.

7. The method of claim 1, wherein the first recurring basis is longer than the second recurring basis.

8. An implantable medical device (IMD), comprising:
   a plurality of electrodes;
   a memory storing an electrode vector parameter indicating an electrode vector of a plurality of electrode vectors, each of the electrode vectors being a different combination of the electrodes;
   a telemetry unit; and
   a processor configured to:
      use the plurality of electrode vectors to generate a plurality of intrathoracic impedance measurements;
      perform a vector selection operation on a first recurring basis, wherein each time the processor performs the vector selection operation, the processor:
         selects a given electrode vector from among the plurality of electrode vectors, the intrathoracic impedance measurements generated using the given electrode vector being at a current time likely to be more reliable than the intrathoracic impedance measurements generated using other ones of the electrode vectors for determining a risk of a patient experiencing a heart failure decompensation event in the near future;

causes the telemetry unit to transmit a vector suggestion message to a programmer after the selection of the given electrode vector, the vector suggestion message specifying the selected electrode vector, wherein the telemetry unit receives a selection message from the programmer in response to the vector suggestion message, the selection message specifying the selected electrode vector or another one of the electrode vectors;

responsive to the selection message, updates the electrode vector parameter to indicate the electrode vector specified by the selection message; and perform a risk assessment operation on a second recurring basis, wherein each time the processor performs the risk assessment operation, the processor determines the risk based at least in part on intrathoracic impedance measurements generated using the electrode vector indicated by the electrode vector parameter, wherein the processor is further configured to:

calculate, based on the intrathoracic impedance measurements generated using the electrode vector indicated by the electrode vector parameter, an initial risk score during the risk assessment operation, the risk score being correlated with a likelihood of the patient experiencing the heart failure decompensation event in the near future;

recalculate the risk score using one or more intrathoracic impedance measurements generated using electrode vectors other than the electrode vector indicated by the electrode vector parameter; and responsive to determining that one of, but not both of, the initial risk score and the recalculated risk score exceeds a predetermined risk threshold, perform the vector selection operation.

9. The IMD of claim 8, wherein when the processor performs the vector selection operations, the processor:
assigns vector scores to the electrode vectors;
ranks the electrode vectors based on the vector scores assigned to the electrode vectors; and
selects the given electrode vector when the given electrode vector is a highest-ranked electrode vector.

10. The IMD of claim 9, wherein when the processor assigns the vector scores to the electrode vectors, the processor assigns the vector scores to the electrode vectors based at least in part on signal-to-noise ratios of the electrode vectors.

11. The IMD of claim 9, wherein when the processor performs the vector selection operation, the processor:
determines whether there is a tie among top-ranked ones of the electrode vectors; and
after determining that there is a tie among the top-ranked electrode vectors, selects one of the top-ranked electrode vectors based on a default ranking of the electrode vectors.

12. The IMD of claim 8, wherein when the processor performs the vector selection operation, the processor:
selects a first electrode vector from among the plurality of electrode vectors;
after selecting the first electrode vector, determines whether the first electrode vector has one or more disqualifying characteristics; and selects a second electrode vector from among the plurality of electrode vectors after determining that the first electrode vector has one or more disqualifying characteristics.

13. The IMD of claim 8, wherein when the processor performs the vector selection operation on a first recurring basis, the processor performs the vector selection operation whenever a recurrence time interval expires.

14. The IMD of claim 8, wherein the first recurring basis is longer than the second recurring basis.

15. A non-transitory computer readable medium that stores instructions, execution of the instructions causing an implantable medical device (IMD) to:
store an electrode vector parameter indicating an electrode vector of a plurality of electrode vectors, each of the electrode vectors being a different combination of electrodes;
use the plurality of electrode vectors to generate a plurality of intrathoracic impedance measurements;
perform a vector selection operation on a first recurring basis, wherein each time the medical device performs the vector selection operation, the medical device:
selects a given electrode vector from among the plurality of electrode vectors, the intrathoracic impedance measurements generated using the given electrode vector being at a current time likely to be more reliable than the intrathoracic impedance measurements generated using other ones of the electrode vectors for determining a risk of a patient experiencing a heart failure decompensation event in the near future;
causes a telemetry unit of the medical device to transmit a vector suggestion message to a programmer after the selection of the given electrode vector, the vector suggestion message specifying the selected electrode vector;
receives a selection message from the programmer in response to the vector suggestion message, the selection message specifying the selected electrode vector or another one of the electrode vectors; and
responsive to the selection message, updates the electrode vector parameter to indicate the electrode vector specified by the selection message;
perform a risk assessment operation on a second recurring basis, wherein each time the medical device performs the risk assessment operation, the medical device determines the risk based at least in part on intrathoracic impedance measurements generated using the electrode vector indicated by the electrode vector parameter;
calculate, based on the intrathoracic impedance measurements generated using the electrode vector indicated by the electrode vector parameter, an initial risk score during the risk assessment operation, the risk score being correlated with a likelihood of the patient experiencing the heart failure decompensation event in the near future;
recalculate the risk score using one or more intrathoracic impedance measurements generated using electrode vectors other than the electrode vector indicated by the electrode vector parameter; and
responsive to determining that one of, but not both of, the initial risk score and the recalculated risk score exceeds a predetermined risk threshold, perform the vector selection operation.

* * * * *